(12) United States Patent
Brenner

(10) Patent No.: US 7,407,757 B2
(45) Date of Patent: Aug. 5, 2008

US007407757B2

(54) GENETIC ANALYSIS BY SEQUENCE-SPECIFIC SORTING

(75) Inventor: Sydney Brenner, Ely (GB)

(73) Assignee: Population Genetics Technologies, Cambridge (GB)

( * ) Notice: Subject to any disclaimer, the term of this patent is extended or adjusted under 35 U.S.C. 154(b) by 349 days.

(21) Appl. No.: 11/173,465

(22) Filed: Jun. 30, 2005

(65) Prior Publication Data

US 2006/0177832 A1 Aug. 10, 2006

Related U.S. Application Data

(63) Continuation-in-part of application No. 11/055,187, filed on Feb. 10, 2005, now Pat. No. 7,217,522.

(60) Provisional application No. 60/662,167, filed on Mar. 16, 2005.

(51) Int. Cl.
*C12Q 1/68* (2006.01)
*C12P 19/34* (2006.01)

(52) U.S. Cl. .......................... 435/6; 435/91.1

(58) Field of Classification Search .............. None
See application file for complete search history.

(56) References Cited

U.S. PATENT DOCUMENTS

| 4,321,365 | A | 3/1982 | Wu et al. ............... 536/24.2 |
|---|---|---|---|
| 5,093,245 | A | 3/1992 | Keith et al. ............. 435/91.2 |
| 5,102,785 | A | 4/1992 | Livak et al. ................. 435/6 |
| 5,149,625 | A | 9/1992 | Church et al. ............... 435/6 |
| 5,401,632 | A | 3/1995 | Wang et al. ................. 435/6 |
| 5,424,186 | A | 6/1995 | Fodor et al. ................. 435/6 |
| 5,445,934 | A | 8/1995 | Fodor et al. ................. 435/6 |
| 5,484,701 | A | 1/1996 | Cocuzza et al. ............. 435/6 |
| 5,503,980 | A | 4/1996 | Cantor ........................ 435/6 |
| 5,508,169 | A | 4/1996 | Deugau et al. .............. 435/6 |
| 5,599,675 | A | 2/1997 | Brenner ...................... 435/6 |
| 5,599,921 | A | 2/1997 | Sorge et al. ............ 536/24.33 |
| 5,631,134 | A | 5/1997 | Cantor ........................ 435/6 |
| 5,635,400 | A | 6/1997 | Brenner ................. 435/320.1 |
| 5,695,934 | A | 12/1997 | Brenner ...................... 435/6 |
| 5,714,330 | A | 2/1998 | Brenner ...................... 435/6 |
| 5,744,305 | A | 4/1998 | Fodor et al. ................. 435/6 |
| 5,759,778 | A | 6/1998 | Li et al. ...................... 435/6 |
| 5,763,175 | A | 6/1998 | Brenner ...................... 435/6 |
| 5,846,719 | A | 12/1998 | Brenner et al. .............. 435/6 |
| 5,876,936 | A | 3/1999 | Ju .............................. 435/6 |
| 5,916,810 | A | 6/1999 | Jarvik ...................... 435/440 |
| 5,935,793 | A | 8/1999 | Wong ......................... 435/6 |
| 6,007,987 | A | 12/1999 | Cantor et al. ................ 435/6 |
| 6,013,445 | A | 1/2000 | Albrecht et al. ............. 435/6 |
| 6,023,540 | A | 2/2000 | Walt et al. ................. 385/12 |
| 6,046,005 | A | 4/2000 | Ju et al. ...................... 435/6 |
| 6,054,270 | A | 4/2000 | Southern .................... 435/6 |
| 6,060,240 | A | 5/2000 | Kamb et al. ................. 435/6 |
| 6,060,596 | A | 5/2000 | Lerner et al. ............. 536/25.3 |
| 6,103,474 | A | 8/2000 | Dellinger et al. ............ 435/6 |
| 6,124,092 | A | 9/2000 | O'Neill et al. .............. 435/6 |
| 6,171,797 | B1 | 1/2001 | Perbost et al. .............. 435/6 |
| 6,261,782 | B1 | 7/2001 | Lizardi et al. ............... 435/6 |
| 6,280,950 | B1 | 8/2001 | Lipshutz et al. ............. 435/6 |
| 6,287,762 | B1 | 9/2001 | Crouzet et al. .............. 435/6 |
| 6,287,778 | B1 | 9/2001 | Huang et al. ................ 435/6 |
| 6,287,825 | B1 | 9/2001 | Weissman et al. ........... 435/6 |
| 6,323,043 | B1 | 11/2001 | Caren et al. ............... 436/518 |
| 6,348,313 | B1 | 2/2002 | Sibson ....................... 435/6 |
| 6,355,431 | B1 | 3/2002 | Chee et al. .................. 435/6 |
| 6,355,432 | B1 | 3/2002 | Fodor et al. ................. 435/6 |
| 6,383,754 | B1 | 5/2002 | Kaufman et al. ............ 435/6 |
| 6,440,667 | B1 | 8/2002 | Fodor et al. ................. 435/6 |
| 6,440,677 | B2 | 8/2002 | Lipshutz et al. ............. 435/6 |
| 6,458,530 | B1 | 10/2002 | Morris et al. ................ 435/6 |
| 6,468,749 | B1 | 10/2002 | Ulanovsky et al. .......... 435/6 |
| 6,514,699 | B1 | 2/2003 | O'Neill et al. .............. 435/6 |
| 6,544,739 | B1 | 4/2003 | Fodor et al. ................. 435/6 |
| 6,573,338 | B2 | 6/2003 | Halverson et al. ......... 525/375 |
| 6,677,121 | B2 | 1/2004 | Lizardi et al. ............... 435/6 |
| 6,773,886 | B2 | 8/2004 | Kaufman et al. ............ 435/6 |

(Continued)

OTHER PUBLICATIONS

Brenner, et al, "In vitro cloning of complex mixtures of DNA on microbeads: Physical separation of differentially expressed cDNAs," Proc. Natl. Acad. Sci., 97: 1665-1670 (2000).

(Continued)

*Primary Examiner*—James Martinell
(74) *Attorney, Agent, or Firm*—David C. Sherer; Carol L. Francis; Bozicevic, Field & Francis LLP

(57) ABSTRACT

The invention provides methods for sorting polynucleotides from a population based on predetermined sequence characteristics. In one aspect, the method of the invention is carried out by extending a primer annealed polynucleotides having predetermined sequence characteristics to incorporate a predetermined terminator having a capture moiety, capturing polynucleotides having extended primers by a capture agent that specifically binds to the capture moiety, and melting the captured polynucleotides from the extended primers to form a subpopulation of polynucleotides having the predetermined sequence characteristics. In another aspect, the method of the invention is carried out on a population of tagged polynucleotides so that after a subpopulation is selected, the members of the subpopulation may be simultaneously analyzed using the unique tags on the polynucleotides to convey analytical information to a hybridization array for a readout.

18 Claims, 14 Drawing Sheets

U.S. PATENT DOCUMENTS

| | | | |
|---|---|---|---|
| 6,958,225 B2 | 10/2005 | Dong | 435/91.2 |
| 7,217,522 B2 * | 5/2007 | Brenner | 435/6 |
| 2003/0003490 A1 | 1/2003 | Fan | 435/6 |
| 2003/0032020 A1 | 2/2003 | Brenner | 435/6 |
| 2003/0049616 A1 | 3/2003 | Brenner et al. | 435/6 |
| 2003/0143580 A1 | 7/2003 | Straus | |
| 2003/0207300 A1 | 11/2003 | Matray et al. | 435/6 |
| 2003/0232348 A1 | 12/2003 | Jones et al. | 435/6 |
| 2004/0086914 A1 | 5/2004 | Cole et al. | 435/6 |
| 2004/0132056 A1 | 7/2004 | Su et al. | 435/6 |
| 2004/0259118 A1 | 12/2004 | Macevicz | 435/6 |
| 2005/0003558 A1 | 1/2005 | Zuckermann et al. | 436/518 |
| 2005/0095645 A1 | 5/2005 | Jones et al. | 435/6 |
| 2005/0142577 A1 | 6/2005 | Jones et al. | 435/6 |

OTHER PUBLICATIONS

Brenner, et al, "Gene Expression Analysis by Massively Parallel Signature Sequencing (MPSS) On Microbead Arrays", Nature Biotechnology (2000) 18:630-634.

Czarnik, A.W., "Encoding Methods for Combinatorial Chemistry", Current Opinion in Chemical Biology (1997) 1:60-66.

Fan, et al, "Parallel Genotyping of Human SNPs Using Generic High-density Oligonucleotide Tag Arrays", Genome Research (2000) 10:853-860.

Fan, et al, "A Versatile Assay for High-Throughput Gene Expression Profiling on Universal Array Matrices", Genome Research (2004) 14:878-885.

Gerry, et al, "Universal DNA Microarray Method for Multiplex Detection of Low Abundance Point Mutations", J. Mol. Biol. (1999) 292:251-262.

Ju, "DNA sequencing with solid-phase-capturable dideoxynucleotides and energy transfer primers," Anal. Biochem., 309: 35-39 (2002).

Hirschhorn, et al, "SBE-TAGS: An Array-based Method for Efficient Single-Nucleotide Polymorphism Genotyping", Proc. Natl. Acad. Sci. (2000) 97:12164-12169.

Hughes, et al, "Expression Profiling Using Microarrays Fabricated by an Ink-jet Oligonucleotide Synthesizer", Nature Biotechnology (2001) 19:342-347.

Charnock-Jones et al, "Extension of incomplete cDNAs (ESTs) by biotin/streptavidin-mediated walking using the polymerase chain reaction," J. Biotechnology, 35: 205-215 (1994).

Schluep et al, "Purification of plasmids by triplex affinity interaction," Nucleic Acids Research, 26: 4524-4528 (1998).

Jordan et al, "Genome complexity reduction for SNP genotyping analysis," Proc. Natl. Acad. Sci., 99: 2942-2947 (2002).

Padgett and Sorge, "Creating seamless junctions independent of restriction sites in PCR cloning." Gene, 168: 31-35 (1996).

Delios et al, "Separation of complementary strands of plasmid DNA using the biotin-avidin system and its application to heteroduplex formation and RNA/DNA hybridizations in electron microscopy," Nucleic Acids Research, 13: 5457-5469 (1985).

Kandpal et al, "Selective enrichment of a large size genomic DNA fragment by affinity capture: an approach for genome mapping," Nucleic Acids Research, 18: 1789-1795F (1990).

* cited by examiner

Combinatorial Tag With No "Commas"

Combinatorial Tag With "Commas" Between Words

Combinatorial Tag With "Commas" at Each End

Combinatorial Tag With "Commas-less" Property

|       |       |       |       |       | Melting Temperatue | | |
|-------|-------|-------|-------|-------|-------|-------|-------|
|       |       |       |       |       | Basic | Salt Adjusted | Nearest Neighbor |
| gtcta | tgtca | cttgt | tcitt | acaga | 53 | 61 | 52 |
|       |       |       |       |       |    |    |    |
| tgtca | tgtca | cttgt | tcitt | acaga | 53 | 61 | 54 |
| acaga | tgtca | cttgt | tcitt | acaga | 53 | 61 | 54 |
| cagaa | tgtca | cttgt | tcitt | acaga | 53 | 61 | 53 |
| aicat | tgtca | cttgt | tcitt | acaga | 51 | 59 | 52 |
| gaact | tgtca | cttgt | tcitt | acaga | 53 | 61 | 53 |
| cttgt | tgtca | cttgt | tcitt | acaga | 53 | 61 | 53 |
| tcitt | tgtca | cttgt | tcitt | acaga | 51 | 59 | 52 |
|       |       |       |       |       |    |    |    |
| gtcta | gtcta | cttgt | tcitt | acaga | 53 | 61 | 52 |
| gtcta | acaga | cttgt | tcitt | acaga | 53 | 61 | 52 |
| gtcta | cagaa | cttgt | tcitt | acaga | 53 | 61 | 52 |
| gtcta | aicat | cttgt | tcitt | acaga | 51 | 59 | 51 |
| gtcta | gaact | cttgt | tcitt | acaga | 53 | 61 | 53 |
| gtcta | cttgt | cttgt | tcitt | acaga | 53 | 61 | 52 |
| gtcta | tcitt | cttgt | tcitt | acaga | 51 | 59 | 51 |
|       |       |       |       |       |    |    |    |
| gtcta | tgtca | gtcta | tcitt | acaga | 53 | 61 | 52 |
| gtcta | tgtca | tgtca | tcitt | acaga | 53 | 61 | 52 |
| gtcta | tgtca | acaga | tcitt | acaga | 53 | 61 | 52 |
| gtcta | tgtca | cagaa | tcitt | acaga | 53 | 61 | 52 |
| gtcta | tgtca | aicat | tcitt | acaga | 51 | 59 | 51 |
| gtcta | tgtca | gaact | tcitt | acaga | 53 | 61 | 53 |
| gtcta | tgtca | tcitt | tcitt | acaga | 51 | 59 | 51 |
|       |       |       |       |       |    |    |    |
| gtcta | tgtca | cttgt | gtcta | acaga | 54 | 63 | 54 |
| gtcta | tgtca | cttgt | tgtca | acaga | 54 | 63 | 54 |
| gtcta | tgtca | cttgt | acaga | acaga | 54 | 63 | 54 |
| gtcta | tgtca | cttgt | cagaa | acaga | 54 | 63 | 54 |
| gtcta | tgtca | cttgt | aicat | acaga | 53 | 61 | 52 |
| gtcta | tgtca | cttgt | gaact | acaga | 54 | 63 | 54 |
| gtcta | tgtca | cttgt | cttgt | acaga | 54 | 63 | 54 |
|       |       |       | Mean  |       | 53 | 61 | 53 |
|       |       |       | Std Dev |     | 1  | 1  | 1  |

Fig. 4

SEQUENCE LISTING

<160> NUMBER OF SEQ ID NOS: 25

<210> SEQ ID NO 1
<211> LENGTH: 15
<212> TYPE: DNA
<213> ORGANISM: Unknown
<220> FEATURE:
<223> OTHER INFORMATION: Probe

<400> SEQUENCE: 1
agtctactgg tttca                                                       15

<210> SEQ ID NO 2
<211> LENGTH: 23
<212> TYPE: DNA
<213> ORGANISM: Unknown
<220> FEATURE:
<223> OTHER INFORMATION: Probe

<400> SEQUENCE: 2
gggttggggt ttacccttt agc                                               23

<210> SEQ ID NO 3
<211> LENGTH: 20
<212> TYPE: DNA
<213> ORGANISM: Unknown
<220> FEATURE:
<223> OTHER INFORMATION: Adaptor

<400> SEQUENCE: 3
tattagctta cttggcctta                                                  20

<210> SEQ ID NO 4
<211> LENGTH: 26
<212> TYPE: DNA
<213> ORGANISM: Unknown
<220> FEATURE:
<223> OTHER INFORMATION: Probe

<400> SEQUENCE: 4
agtctactgg tttcaattaa ttaatt                                           26

<210> SEQ ID NO 5
<211> LENGTH: 23
<212> TYPE: DNA
<213> ORGANISM: Unknown

```
<220> FEATURE:
<223> OTHER INFORMATION: Probe

<400> SEQUENCE: 5
gggttggggt ttaccccttt agc                                              23

<210> SEQ ID NO 6
<211> LENGTH: 15
<212> TYPE: DNA
<213> ORGANISM: Unknown
<220> FEATURE:
<223> OTHER INFORMATION: Probe

<400> SEQUENCE: 6
tcagatgacc aaagt                                                       15

<210> SEQ ID NO 7
<211> LENGTH: 30
<212> TYPE: DNA
<213> ORGANISM: Unknown
<220> FEATURE:
<223> OTHER INFORMATION: Probe

<400> SEQUENCE: 7
tcagatgacc aaagttcaga tgaccaaagt                                       30

<210> SEQ ID NO 8
<211> LENGTH: 10
<212> TYPE: DNA
<213> ORGANISM: Unknown
<220> FEATURE:
<223> OTHER INFORMATION: Probe

<400> SEQUENCE: 8
cccttagctg                                                             10

<210> SEQ ID NO 9
<211> LENGTH: 31
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: (6)..(26)
<223> OTHER INFORMATION: n is a, c, g, or t

<400> SEQUENCE: 9
gcatcnnnnn nnnnnnnnnn nnnnnncatc c                                     31

<210> SEQ ID NO 10
<211> LENGTH: 16
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: (6)..(16)
<223> OTHER INFORMATION: n is a, c, g, or t

<400> SEQUENCE: 10
gcatcnnnnn nnnnnn                                                      16

<210> SEQ ID NO 11
<211> LENGTH: 26
<212> TYPE: DNA
```

```
<213> ORGANISM: Unknown
<220> FEATURE:
<223> OTHER INFORMATION: Adaptor
<220> FEATURE:
<221> NAME/KEY: misc_feature
<222> LOCATION: (2)..(11)
<223> OTHER INFORMATION: n is a, c, g, or t
<220> FEATURE:
<221> NAME/KEY: misc_feature
<222> LOCATION: (17)..(25)
<223> OTHER INFORMATION: n is a, c, g, or t

<400> SEQUENCE: 11
cnnnnnnnnn ngcatcnnnn nnnnna                                  26

<210> SEQ ID NO 12
<211> LENGTH: 65
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (37)..(56)
<223> OTHER INFORMATION: n is a, c, g, or t
<220> FEATURE:
<221> NAME/KEY: misc_feature
<222> LOCATION: (63)..(65)
<223> OTHER INFORMATION: n is a, c, g, or t

<400> SEQUENCE: 12
nnnnggtacc gctcttcgtt gkdddddddd dgtcccnnnn nnnnnnnnnn nnnnnnaggc    60 ctnnn                                                         65

<210> SEQ ID NO 13
<211> LENGTH: 29
<212> TYPE: DNA
<213> ORGANISM: Unknown
<220> FEATURE:
<223> OTHER INFORMATION: Primer
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(24)
<223> OTHER INFORMATION: n is a, c, g, or t

<400> SEQUENCE: 13
nnnaggcctn nnnnnnnnnn nnnngggac                               29

<210> SEQ ID NO 14
<211> LENGTH: 42
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: (2)..(11)
<223> OTHER INFORMATION: n is a, c, g, or t
<220> FEATURE:
<221> NAME/KEY: misc_feature
<222> LOCATION: (17)..(37)
<223> OTHER INFORMATION: n is a, c, g, or t

<400> SEQUENCE: 14
```

-continued cnnnnnnnnn ngcatcnnnn nnnnnnnnnn nnnnnnncat cc    42

<210> SEQ ID NO 15
<211> LENGTH: 51
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: (10)..(31)
<223> OTHER INFORMATION: n is a, c, g, or t
<220> FEATURE:
<221> NAME/KEY: misc_feature
<222> LOCATION: (37)..(46)
<223> OTHER INFORMATION: n is a, c, g, or t

<400> SEQUENCE: 15
gatcggatgn nnnnnnnnnn nnnnnnnnn nctacgnnnn nnnnnngggc c    51

<210> SEQ ID NO 16
<211> LENGTH: 26
<212> TYPE: DNA
<213> ORGANISM: Unknown
<220> FEATURE:
<223> OTHER INFORMATION: Primer
<220> FEATURE:
<221> NAME/KEY: misc_feature
<222> LOCATION: (7)..(21)
<223> OTHER INFORMATION: n is a, c, g, or t

<400> SEQUENCE: 16
aggcctnnnn nnnnnnnnnn ngggac    26

<210> SEQ ID NO 17
<211> LENGTH: 19
<212> TYPE: DNA
<213> ORGANISM: Unknown
<220> FEATURE:
<223> OTHER INFORMATION: Adaptor

<400> SEQUENCE: 17
ccctgkdddd dddddgatc    19

<210> SEQ ID NO 18
<211> LENGTH: 40
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: (20)..(34)
<223> OTHER INFORMATION: n is a, c, g, or t

<400> SEQUENCE: 18
gatckddddd ddddgtcccn nnnnnnnnnn nnnnaggcct    40

<210> SEQ ID NO 19
<211> LENGTH: 40
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: (7)..(21)
<223> OTHER INFORMATION: n is a, c, g, or t
<220> FEATURE:

```
<221> NAME/KEY: 5-methylcytosine
<222> LOCATION: (40)..(40)

<400> SEQUENCE: 19
aggcctnnnn nnnnnnnnnn ngggacdddd ddddkgatc                              40

<210> SEQ ID NO 20
<211> LENGTH: 19
<212> TYPE: DNA
<213> ORGANISM: Unknown
<220> FEATURE:
<223> OTHER INFORMATION: Adaptor
<220> FEATURE:
<221> NAME/KEY: 5-methylcytosine
<222> LOCATION: (4)..(4)
<220> FEATURE:
<221> NAME/KEY: 5-methylcytosine
<222> LOCATION: (17)..(19)

<400> SEQUENCE: 20
gatcdddddd dddkgtccc                                                    19

<210> SEQ ID NO 21
<211> LENGTH: 19
<212> TYPE: DNA
<213> ORGANISM: Unknown
<220> FEATURE:
<223> OTHER INFORMATION: Adaptor

<400> SEQUENCE: 21
gggacddddd dddkgatc                                                     19

<210> SEQ ID NO 22
<211> LENGTH: 27
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: (1)..(20)
<223> OTHER INFORMATION: n is a, c, g, or t
<220> FEATURE:
<221> NAME/KEY: 5-methylcytosine
<222> LOCATION: (22)..(22)

<400> SEQUENCE: 22
nnnnnnnnnn nnnnnnnnnn gcatcag                                           27

<210> SEQ ID NO 23
<211> LENGTH: 17
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t

<400> SEQUENCE: 23
nngcatcaaa agatcnn                                                      17

<210> SEQ ID NO 24
<211> LENGTH: 12
```

-continued

```
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: (1)..(2)
<223> OTHER INFORMATION: n is a, c, g, or t

<400> SEQUENCE: 24
nngcatcaaa ag                                                              12

<210> SEQ ID NO 25
<211> LENGTH: 12
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: (1)..(3)
<223> OTHER INFORMATION: n is a, c, g, or t

<400> SEQUENCE: 25
nnngcatcaa aa                                                              12
```

GENETIC ANALYSIS BY SEQUENCE-SPECIFIC SORTING

This application is a continuation-in-part of U.S. application Ser. No. 11/055,187 filed 10 Feb. 2005 now U.S. Pat. No. 7,217,522 and claims priority from U.S. provisional application Ser. No. 60/662,167 filed 16 Mar. 2005, each of which is incorporated herein by reference in its entirety.

FIELD OF THE INVENTION

The invention relates generally to methods and compositions for analyzing complex populations of polynucleotides, and more particularly, to methods and compositions for partitioning a population of polynucleotides into one or more subpopulations of lesser complexity.

BACKGROUND

A major goal in genetics research is to understand how sequence variations in the genome relate to complex traits, particularly susceptibilities for common diseases such as diabetes, cancer, hypertension, and the like, e.g. Collins et al, Nature, 422: 835-847 (2003). The draft sequence of the human genome has provided a highly useful reference for assessing variation, but it is only a first step towards understanding how the estimated 10 million or more common single nucleotide polymorphisms (SNPs), and other polymorphisms, such as inversions, deletions, insertions, and the like, determine or affect states of health and disease. Many powerful analytical approaches have been developed to address this problem, but none appear to have adequate throughput or flexibility for the types of studies required to associate traits practically and reliably with genomic variation, e.g. Syvanen, Nature Reviews Genetics, 2: 930-942 (2001). For example, it would be desirable to carry out trait-association studies in which a large set of genetic markers from populations of affected and unaffected individuals are compared. Such studies depend on the non-random segregation, or linkage disequilibrium, between the genetic markers and genes involved in the trait or disease being studied. Unfortunately, the extent and distribution of linkage disequilibrium between regions of the human genome is not well understood, but it is currently believed that successful trait-association studies in humans would require the measurement of 30-50,000 markers per individual in populations of at least 300-400 affected individuals and an equal number of controls, Kruglyak and Nickerson, Nature Genetics, 27: 234-236 (2001); Lai, Genome Research, 11: 927-929 (2001); Risch and Merikangas, Science, 273: 1516-1517 (1996); Cardon and Bell, Nature Reviews Genetics, 2: 91-99 (2001).

One approach to dealing with such whole-genome studies is to create subsets of genomic DNA having reduced complexity with respect to the genomes being analyzed in order to simplify the analysis, e.g. Lisitsyn et al, Science, 259: 946-951 (1993); Vos et al, Nucleic Acids Research, 23: 4407-4414 (1995); Dong et al, Genome Research, 11: 1418-1424 (2001); Jordan et al, Proc. Natl. Acad. Sci., 99: 2942-2947 (2002); Weissman et al, U.S. Pat. No. 6,506,562; Sibson, U.S. Pat. No. 5,728,524; Degau et al, U.S. Pat. No. 5,858,656. Unfortunately, most of these techniques rely on some form of subtraction, sequence destruction, or direct or indirect size selection to create subsets, which are difficult to implement and reduce sensitivity.

In view of the above, the field of genetic analysis would be advanced by the availability of a method for converting a highly complex population of DNA, such as a mixture of genomes, into subsets having reduced complexity without requiring subtraction, or other sequence destroying, steps.

SUMMARY OF THE INVENTION

The invention provides methods and compositions for sorting polynucleotides from a population based on predetermined sequence characteristics. In one aspect, the method of the invention is carried out by the following steps: (i) extending a primer annealed polynucleotides having predetermined sequence characteristics to incorporate a predetermined terminator having a capture moiety, (ii) capturing polynucleotides having extended primers by a capture agent that specifically binds to the capture moiety, and (iii) melting the captured polynucleotides from the extended primers to form a subpopulation of polynucleotides having the predetermined sequence characteristics. An exemplary predetermined sequence characteristic is a segment of sequence common to at least one fragment in each of a population of different genomes, such as a segment of an exon, a segment of an intron, a promoter sequence, or the like.

In another aspect, the invention includes as method of determining a subset of polynucleotides in a parent population that have sequences that vary from that of a reference sequence. In one embodiment, such a method comprises the following steps: (a) annealing a primer to polynucleotides of a parent population to form primer-polynucleotide duplexes; (b) extending the primer in the presence of at least one predetermined terminator having a capture moiety, the predetermined terminator being non-complementary with the reference sequence, so that after extension primer-polynucleotide complexes that contain a polynucleotide having a sequence different from that of the reference sequence have capture moieties; (c) separating the primer-polynucleotide duplexes having an extended primer with a capture moiety from the parent population by specifically binding the capture moiety of the predetermined terminator to a capture agent; (d) melting captured primer-polynucleotide duplexes to form a selected population of polynucleotides having sequences different from that of the reference sequence; (e) shortening polynucleotides of the parent population by from 1 to 20 nucleotides to form a new parent population; and (f) repeating steps (a) through (e) until all the polynucleotides of the parent population have been sorted from polynucleotides having sequences identical to the reference sequence.

In another aspect, the population of polynucleotides analyzed by the method of the invention comprises fragments from a population of genomes, wherein the fragments from each genome has the same unique oligonucleotide tag attached. In this aspect, the invention includes a method of determining a frequency of a nucleotide at a predetermined locus in a population of genomes, such method comprising the following steps: (i) separately generating fragments of each genome of the population; (ii) attaching a unique oligonucleotide tag to each genome; (iii) selecting fragments from each genome that contains the predetermined locus; (iv) generating a labeled oligonucleotide tag from each unique oligonucleotide tag, the labeled oligonucleotide tag generating a signal indicative of the nucleotide at the predetermined locus; and (v) determining the frequency of the nucleotide at the predetermined locus by detecting the signals generated by the labeled oligonucleotide tags specifically hybridized with their respective tag complements, the respective tag complements being attached in spatially discrete regions on the one or more solid phase supports.

In another aspect, the invention provides a method of determining a frequency of a nucleotide at a predetermined locus in a population of genomes, the method comprising the steps of: separately generating fragments of each genome of the population; attaching a unique oligonucleotide tag to each genome; selecting fragments from each genome that contains the predetermined locus; generating a labeled oligonucleotide tag from each unique oligonucleotide tag, the labeled oligonucleotide tag generating a signal indicative of the nucleotide at the predetermined locus; and determining the frequency of the nucleotide at the predetermined locus by detecting the signals generated by the labeled oligonucleotide tags specifically hybridized with their respective tag complements, the respective tag complements being attached in spatially discrete regions on the one or more solid phase supports.

BRIEF DESCRIPTION OF THE DRAWINGS

FIG. 4 lists melting temperatures of selected tags consisting of four words each having the comma-less property.

DEFINITIONS

Figure 1A:
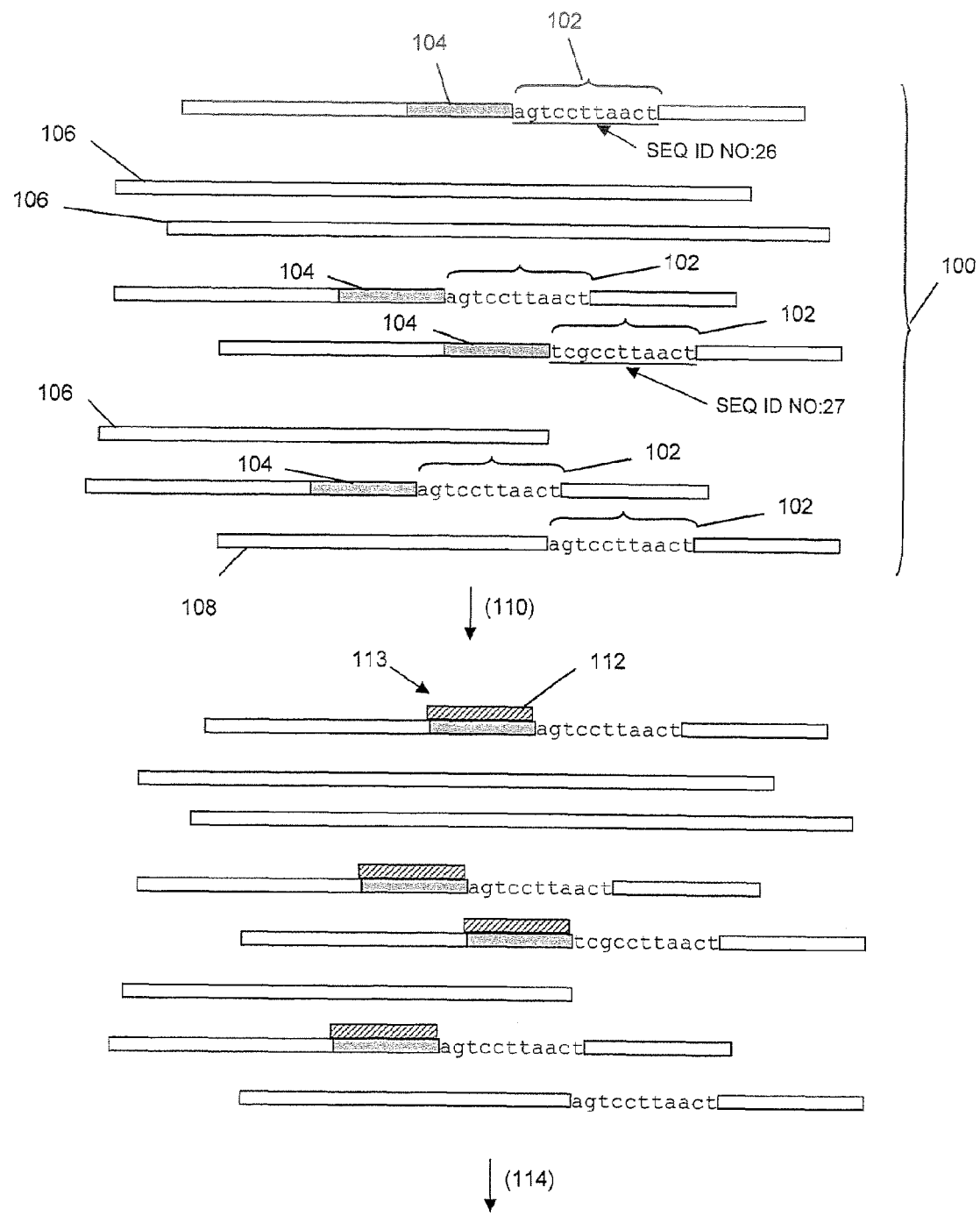
FIGS. 1A-1F illustrate the selection of particular fragments by common sequence elements.

Terms and symbols of nucleic acid chemistry, biochemistry, genetics, and molecular biology used herein follow those of standard treatises and texts in the field, e.g. Kornberg and Baker, DNA Replication, Second Edition (W. H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

"Addressable" in reference to tag complements means that the nucleotide sequence, or perhaps other physical or chemical characteristics, of a tag complement can be determined from its address, i.e. a one-to-one correspondence between the sequence or other property of the tag complement and a spatial location on, or characteristic of, the solid phase support to which it is attached. Preferably, an address of a tag complement is a spatial location, e.g. the planar coordinates of a particular region containing copies of the tag complement. However, tag complements may be addressed in other ways too, e.g. by microparticle size, shape, color, frequency of micro-transponder, or the like, e.g. Chandler et al, PCT publication WO 97/14028.

"Allele frequency" in reference to a genetic locus, a sequence marker, or the site of a nucleotide means the frequency of occurrence of a sequence or nucleotide at such genetic loci or the frequency of occurrence of such sequence marker, with respect to a population of individuals. In some contexts, an allele frequency may also refer to the frequency of sequences not identical to, or exactly complementary to, a reference sequence.

"Amplicon" means the product of an amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced in a polymerase chain reaction (PCR), by replication in a cloning vector, or by linear amplification by an RNA polymerase, such as T7 or SP6, or by like techniques.

"Analyte" means any molecule, including organic, inorganic, or biomolecule, whose presence or absence or quantity or concentration in a sample is to be determined in an assay. In one aspect, analytes are oligonucleotides, polynucleotides, genomic fragments, messenger RNAs (mRNAs), proteins, antibodies, enzymes, complementary DNAs (cDNAs), and like compounds. In another aspect, analytes are genomic fragments, particularly human genomic fragments.

"Complement" or "tag complement" as used herein in reference to oligonucleotide tags refers to an oligonucleotide to which an oligonucleotide tag specifically hybridizes to form a perfectly matched duplex or triplex. In embodiments where specific hybridization results in a triplex, the oligonucleotide tag may be selected to be either double stranded or single stranded. Thus, where triplexes are formed, the term "complement" is meant to encompass either a double stranded complement of a single stranded oligonucleotide tag or a single stranded complement of a double stranded oligonucleotide tag.

"Complexity" in reference to a population of double stranded or single stranded polynucleotides means the number of different species of polynucleotide present in the population. The related concept, "kinetic complexity" in reference to genomic DNA means the total number of basepairs present in non-repeating sequences, e.g. Wetmur, Critical Reviews in Biochemistry and Molecular Biology, 26: 227-259 (1991); Britten and Davidson, chapter 1 in Hames et al, editors, Nucleic Acid Hybridization: A Practical Approach (IRL Press, Oxford, 1985). For example, the following populations have the indicated sizes and complexities:

| Population | Population Size | Complexity |
|---|---|---|
| agtctactggtttca | 3 | 3 |
| tcagatgaccaaagt (SEQ ID NO: 1) | | |
| gggttggggtttaccccttttagc | | |
| cccaaccccaaatggggaaatcg (SEQ ID NO: 2) | | |
| tattagcttacttggcctta | | |
| ataatcgaatgaaccggaat (SEQ ID NO: 3) | | |
| agtctactggttttcaattaattaatt | 2 | 2 |
| tcagatgaccaaagttaattaattaa (SEQ ID NO: 4) | | |
| gggttggggtttaccccttttagc | | |
| cccaaccccaaatggggaaatcg (SEQ ID NO: 2) | | |
| gggttggggtttaccccttttagc (SEQ ID NO: 5) | 5 | 3 |
| tcagatgaccaaagt (SEQ ID NO: 6) | | |
| tcagatgaccaaagt (SEQ ID NO: 6) | | |

-continued

| Population | Population Size | Complexity |
|---|---|---|
| tcagatgaccaaagt (SEQ ID NO: 6) | | |
| tcagatgaccaaagttcagatgaccaaagt (SEQ ID NO: 7) | | |
| cccttagctg       agggct (SEQ ID NO: 8) | 8 | 3 |
| cccttagctg       agggct (SEQ ID NO: 8) | | |
| cccttagctg       agggct (SEQ ID NO: 8) | | |
| cccttagctg       agggct (SEQ ID NO: 8) | | |
| cccttagctg       agggctc (SEQ ID NO: 8) | | |

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. In one aspect, stable duplex means that a duplex structure is not destroyed by a stringent wash, e.g. conditions including tempature of about 5° C. less that the $T_m$ of a strand of the duplex and low monovalent salt concentration, e.g. less than 0.2 M, or less than 0.1 M. "Perfectly matched" in reference to a duplex means that the poly- or oligonucleotide strands making up the duplex form a double stranded structure with one another such that every nucleotide in each strand undergoes Watson-Crick basepairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding. "Melting" as used herein means de-annealing. That is, melting means the destabilization of a duplex so that the strands of the duplex separate and become independent single stranded polynucleotides. Melting is usually accomplished by raising the temperature of a reaction mixture to a level above the melting temperature of the duplex. Melting can also be accomplished by adding denaturants, such as urea, sodium hydroxide, or other bases, or organic solvents, such as formamide.

"Fragment", "segment", or "DNA segment" refers to a portion of a larger DNA polynucleotide or DNA. A polynucleotide, for example, can be broken up, or fragmented into, a plurality of segments. Various methods of fragmenting nucleic acid are well known in the art. These methods may be, for example, either chemical or physical or enzymatic in nature. Enzymatic fragmentation may include partial degradation with a DNase; partial depurination with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave DNA at known or unknown locations. Physical fragmentation methods may involve subjecting the DNA to a high shear rate. High shear rates may be produced, for example, by moving DNA through a chamber or channel with pits or spikes, or forcing the DNA sample through a restricted size flow passage, e.g., an aperture having a cross sectional dimension in the micron or submicron scale. Other physical methods include sonication and nebulization. Combinations of physical and chemical fragmentation methods may likewise be employed such as fragmentation by heat and ion-mediated hydrolysis. See for example, Sambrook et al., "Molecular Cloning: A Laboratory Manual," $3^{rd}$ Ed. Cold Spring Harbor Laboratory Press, Cold Spring Harbor, N.Y. (2001) ("Sambrook et al.") which is incorporated herein by reference for all purposes. These methods can be optimized to digest a nucleic acid into fragments of a selected size range.

"Genetic locus," or "locus" in reference to a genome or target polynucleotide, means a contiguous subregion or segment of the genome or target polynucleotide. As used herein, genetic locus, or locus, may refer to the position of a nucleotide, a gene, or a portion of a gene in a genome, including mitochondrial DNA, or it may refer to any contiguous portion of genomic sequence whether or not it is within, or associated with, a gene. In one aspect, a genetic locus refers to any portion of genomic sequence, including mitochondrial DNA, from a single nucleotide to a segment of few hundred nucleotides, e.g. 100-300, in length. Usually, a particular genetic locus may be identified by its nucleotide sequence, or the nucleotide sequence, or sequences, of one or both adjacent or flanking regions.

"Haplotype" means a series of alleles found at linked loci on a single chromosome. More particularly, haplotype means a series of single nucleotide polymorphisms at predetermined loci in a genomic DNA fragment.

"Hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1M, more usually less than about 500 mM and less than about 200 mM. Hybridization temperatures can be as low as 5° C., but are typically greater than 22° C., more typically greater than about 30° C., and preferably in excess of about 37° C. Hybridizations are usually performed under stringent conditions, i.e. conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at s defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see for example, Sambrook, Fritsche and Maniatis. "Molecular Cloning A laboratory Manual" $2^{nd}$ Ed. Cold Spring Harbor Press (1989) and Anderson "Nucleic Acid Hybridization" $1^{st}$ Ed., BIOS Scientific Publishers Limited (1999), which are hereby incorporated by reference in its entirety for all purposes above. "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whitely et al, U.S. Pat. No. 4,883,750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al, Methods in Enzymology, 68: 50-71 (1979); Engler et al, The Enzymes, 15: 3-29 (1982); and Namsaraev, U.S. patent publication 2004/0110213.

"Microarray" refers to a solid phase support, which may be planar or a collection of microparticles, that carries or carry oligo- or polynucleotides fixed or immobilized, usually covalently, at specific addressable locations. Preferably, a microarray is a solid phase support having a planar surface, which carries an array of nucleic acids, each member of the array comprising identical copies of an oligonucleotide or polynucleotide immobilized to a fixed region, which does not overlap with those of other members of the array. Typically, the oligonucleotides or polynucleotides are single stranded and are covalently attached to the solid phase support at known, determinable, or addressable, locations. The density of non-overlapping regions containing nucleic acids in a microarray is typically greater than 100 per $cm^2$, and more preferably, greater than 1000 per $cm^2$. Microarray technology is reviewed in the following references: Schena, Editor, Microarrays: A Practical Approach (IRL Press, Oxford, 2000); Southern, Current Opin. Chem. Biol., 2: 404-410 (1998); Nature Genetics Supplement, 21: 1-60 (1999).

"Nucleoside" as used herein includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al, Exp. Opin. Ther. Patents, 6: 855-870 (1996); Mesmaeker et al, Current Opinion in Structural Biology, 5: 343-355 (1995); and the like. Exemplary types of polynucleotides that are capable of enhancing duplex stability include oligonucleotide N3'→P5' phosphoramidates (referred to herein as "amidates"), peptide nucleic acids (referred to herein as "PNAs"), oligo-2'-O-alkylribonucleotides, polynucleotides containing C-5 propynylpyrimidines, and like compounds. Such oligonucleotides are either available commercially or may be synthesized using methods described in the literature.

"Oligonucleotide tag" means an oligonucleotide that is attached to a polynucleotide and is used to identify and/or track the polynucleotide in a reaction. Usually, a oligonucleotide tag is attached to the 3'- or 5'-end of a polynucleotide to form a linear conjugate, sometime referred to herein as a "tagged polynucleotide." Oligonucleotide tags may vary widely in size and compositions; the following references provide guidance for selecting sets of oligonucleotide tags appropriate for particular embodiments: Brenner, U.S. Pat. No. 5,635,400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981,179; and the like. In aspects of the invention, oligonucleotide tags each have a length within a range of from 4 to 36 nucleotides, or from 6 to 30 nucleotides, or from 8 to 20 nucleotides, respectively. In another aspect, oligonucleotide tags are used in sets, or repertoires, wherein each oligonucleotide tag of the set has a unique nucleotide sequence. In a further aspect, each oligonucleotide tag of such a set has a melting temperature that is substantially the same as that of every other member of the same set. In such aspects, the melting temperatures of oligonucleotide tags within a set are within 10° C. of one another; in another embodiment, they are within 5° C. of one another; and in another embodiment, they are within 2° C. of one another. In another aspect, oligonucleotide tags within a set are maximally orthogonal. That is, they minimally cross-hybridize to their respective complements. In one aspect, oligonucleotide tags within a set have at least one mismatch when hybridized to any complement of other members of the same set; in another aspect, oligonucleotide tags within a set have at least two mismatches when hybridized to any complement of other members of the same set; in another aspect, oligonucleotide tags within a set have at least three mismatches when hybridized to any complement of other members of the same set; in another aspect, oligonucleotide tags within a set have at least four mismatches when hybridized to any complement of other members of the same set; in another aspect, oligonucleotide tags within a set have at least five mismatches when hybridized to any complement of other members of the same set. The properties of minimal cross-hybridization, or equivalently, maximal orthogonality, within a set of oligonucleotide tags is especially useful when oligonucleotide tags are identified by a hybridization reation, such as by hybridizing a labeled oligonucleotide tag to its complement on a solid phase support. The size of such sets may vary widely. A set of oligonucleotide tags may have a size in the range of from several tens to many thousands, or even millions, e.g. 50 to $1.6 \times 10^6$. In another embodiment, such a size is in the range of from 200 to 40,000; or from 1000 to 40,000; or from 1000 to 10,000. In another aspect of the invention, oligonucletide tags may comprise a concatenation of subunits, such as described by Brenner et al, Proc. Natl. Acad. Sci., 97: 1665-1670 (2000). In such concatenates, oligonucleotide subunits, or words, can be selected from a set of subunits with the properties of minimal cross-hybridization and substantially equivalent melting temperature. Constructing oligonucleotide tags from a plurality of oligonucleotide subunits permits the convenient and inexpensive formation of very large sets of oligonucleotide tags, e.g. as described by Brenner et al, Proc. Natl. Acad. Sci., 97: 1665-1670 (2000). Also, the use of oligonucleotide subunits permits enzymatic synthesis and/or attachment of oligonucleotide tags to polynucleotides, e.g. as described below and in Brenner and Williams, U.S. patent publication 2003/0049616. In one aspect, oligonucleotide tags comprise a plurality of oligonucleotide subunits. Such subunits may vary widely in length. In one aspect, the length of oligonucleotide subunits is in the range of from 2 to 18 nucleotides; in another aspect, the length of oligonucleotide subunits is in the range of from 2 to 8 nucleotides; and in another aspect the length of oligonucleotide subunits is in the range of from 2 to 4 nucleotides. A plurality of oligonucleotide subunits making up an oligonucleotide tag may also vary widely depending on their application. In one aspect, such plurality is a number in the range of 2 to 10; and in another aspect, such plurality is a number in the range of from 2 to 6. The size of a set of oligonucleotide subunits is usually smaller than the size of a set of oligonucleotide tags. Usually, a set of oligonucleotide subunits has a size in the range of from 2 to 20; or in another embodiment, from 2 to 10; or in another embodiment, from 4 to 8. It is clear to one of ordinary skill that for subunits only two nucleotides in length that the size of a set of subunits would be smaller than that of subunits having greater lengths.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred μL, e.g. 200 μL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999) (two-color real-time PCR). Usually, distinct sets of primers are employed for each sequence being amplified. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $\beta_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

"Polymorphism" or "genetic variant" means a substitution, inversion, insertion, or deletion of one or more nucleotides at a genetic locus, or a translocation of DNA from one genetic locus to another genetic locus. In one aspect, polymorphism means one of multiple alternative nucleotide sequences that may be present at a genetic locus of an individual and that may comprise a nucleotide substitution, insertion, or deletion with respect to other sequences at the same locus in the same individual, or other individuals within a population. An individual may be homozygous or heterozygous at a genetic locus; that is, an individual may have the same nucleotide sequence in both alleles, or have a different nucleotide sequence in each allele, respectively. In one aspect, insertions or deletions at a genetic locus comprises the addition or the absence of from 1 to 10 nucleotides at such locus, in comparison with the same locus in another individual of a population (or another allele in the same individual0. Usually, insertions or deletions are with respect to a major allele at a locus within a population, e.g. an allele present in a population at a frequency of fifty percent or greater.

"Polynucleotide" or "oligonucleotide" are used interchangeably and each mean a linear polymer of natural or modified nucleotide monomers. Monomers making up polynucleotides and oligonucleotides include deoxyribonucleotides, ribonucleotides, 2'-deoxy-3'-phosphorothioate nucleosides, peptide nucleic acids (PNAs), and the like, that are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Polynucleotides typically range in size from a few monomeric units, e.g. 5-40, when they are usually referred to as "oligonucleotides," to several thousand monomeric units. Whenever a polynucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA) linked by phosphodiester linkages; however, they may also comprise non-natural nucleotide analogs, e.g. including modified bases, sugars, or internucleosidic linkages. It is clear to those skilled in the art when oligonucleotides having natural or non-natural nucleotides may be employed, e.g. where processing by enzymes is called for, usually polynucleotides consisting solely of natural nucleotides are required. Likewise, where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of from 14 to 36 nucleotides.

"Readout" means a parameter, or parameters, which are measured and/or detected that can be converted to a number or value. In some contexts, readout may refer to an actual numerical representation of such collected or recorded data. For example, a readout of fluorescent intensity signals from a microarray is the address and fluorescence intensity of a signal being generated at each hybridization site of the microarray; thus, such a readout may be registered or stored in various ways, for example, as an image of the microarray, as a table of numbers, or the like.

"Sequence determination" or "determining a nucleotide sequence" in reference to polynucleotides includes determination of partial as well as full sequence information of the polynucleotide. That is, the term includes sequence comparisons, fingerprinting, and like levels of information about a target polynucleotide, as well as the express identification and ordering of nucleosides, usually each nucleoside, in a target polynucleotide. The term also includes the determination of the identity, ordering, and locations of one, two, or three of the four types of nucleotides within a target polynucleotide. For example, in some embodiments sequence determination may be effected by identifying the ordering and locations of a single type of nucleotide, e.g. cytosines, within the target polynucleotide "CATCGC . . . " so that its sequence is represented as a binary code, e.g. "100101 . . . " for "C-(not C)-(not C)-C-(not C)-C . . . " and the like.

"Specific" or "specificity" in reference to the binding of one molecule to another molecule, such as a binding compound, or probe, for a target analyte, means the recognition, contact, and formation of a stable complex between the probe and target, together with substantially less recognition, contact, or complex formation of the probe with other molecules. In one aspect, "specific" in reference to the binding of a first molecule to a second molecule means that to the extent the first molecule recognizes and forms a complex with another molecules in a reaction or sample, it forms the largest number of the complexes with the second molecule. In one aspect, this largest number is at least fifty percent of all such complexes form by the first molecule. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, ionic and hydrophobic interactions, and the like, dominate the interaction of the molecules. As used herein, "stable complex" in reference to two or more molecules means that such molecules form non-covalently linked aggregates, e.g. by specific binding, that under assay conditions are thermodynamically more favorable than a non-aggregated state.

"Spectrally resolvable" in reference to a plurality of fluorescent labels means that the fluorescent emission bands of the labels are sufficiently distinct, i.e. sufficiently non-overlapping, that molecular tags to which the respective labels are attached can be distinguished on the basis of the fluorescent signal generated by the respective labels by standard photodetection systems, e.g. employing a system of band pass filters and photomultiplier tubes, or the like, as exemplified by the systems described in U.S. Pat. Nos. 4,230,558; 4,811,218, or the like, or in Wheeless et al, pgs. 21-76, in Flow Cytometry: Instrumentation and Data Analysis (Academic Press, New York, 1985).

"$T_m$" is used in reference to "melting temperature." Melting temperature is the temperature at which a population of double-stranded nucleic acid molecules becomes half dissociated into single strands. Several equations for calculating the Tm of nucleic acids are well known in the art. As indicated by standard references, a simple estimate of the Tm value may be calculated by the equation. Tm=81.5+0.41 (% G+C), when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr., Biochemistry 36, 10581-94 (1997)) include alternative methods of computation which take structural and environmental, as well as sequence characteristics into account for the calculation of Tm.

"Terminator" means a nucleotide that can be incorporated into a primer by a polymerase extension reaction, wherein the nucleotide prevents subsequent incorporation of nucleotides to the primer and thereby halts polymerase-mediated extension. Typical terminators are nucleoside triphosphates that lack a 3'-hydroxyl substituent and include 2',3'-dideoxyribose, 2',3'-didehydroribose, and 2',3'-dideoxy-3'-haloribose, e.g. 3'-deoxy-3'-fluoro-ribose or 2',3'-dideoxy-3'-fluororibose nucleosides, for example. Alternatively, a ribofuranose analog can be used in terminators, such as 2',3'-dideoxy-β-D-ribofuranosyl, β-D-arabinofuranosyl, 3'-deoxy-β-D-arabinofuranosyl, 3'-arnino-2',3'-dideoxy-β-D-ribofaranosyl, and 2,3'-dideoxy-3'-fluoro-β-D-ribofuranosyl. A variety of terminators are disclosed in the following references: Chidgeavadze et al., Nucleic Acids Res., 12: 1671-1686 (1984); Chidgeavadze et al., FEBS Lett., 183: 275-278 (1985); Izuta et al, Nucleosides & Nucleotides, 15: 683-692 (1996); and Krayevsky et al, Nucleosides & Nucleotides, 7: 613-617 (1988). Nucleotide terminators also include reversible nucleotide terminators, e.g. Metzker et al. Nucleic Acids Res., 22(20):4259 (1994). Terminators of particular interest are terminators having a capture moiety, such as biotin, or a derivative thereof, e.g. Ju, U.S. Pat. No. 5,876,936, which is incorporated herein by reference. As used herein, a "predetermined terminator" is a terminator that basepairs with a desired nucleoside of a template in a reaction extending a primer. For example, in one aspect of the invention, a primer extension step is carried out in each of four different reaction vessels, such that each reaction vessel contains a different terminator. In a first reaction vessel, the terminator base pairs with a deoxyadenosine (i.e., the "desired" nucleoside); in a second reaction vessel, the terminator base pairs with a deoxycytidine; in a third reaction vessel, the terminator base pairs with a deoxyguanosine; and in a fourth reaction vessel, the terminator base pairs with a deoxythymidine.

DETAILED DESCRIPTION OF THE INVENTION

In one aspect, the invention provides methods for sorting polynucleotides based on predetermined sequence characteristics to form subpopulations of reduced complexity. In another aspect, such sorting methods are used to analyze populations of uniquely tagged polynucleotides, such as genome fragments. That is, mixtures may be formed containing fragments of genomic DNA from different individuals such that each individual's DNA is labeled with a unique oligonucleotide tag. During or at the conclusion of repeated steps of sorting in accordance with the invention, the tags may be replicated, labeled and hybridized to a solid phase support, such as a microarray, to provide a simultaneous readout of sequence information related to the genomic DNA. Predetermined sequence characteristics include, but are not limited to, a unique sequence region at a particular locus, or a series of polymorphisms, such as insertions, deletions, or substitutions, at a series of loci, or the like. A predetermined sequence characteristic can be selected from a wide variety of genomic features including, but not limited to, a segment of a selected exon of a selected gene, a selected intron of a selected gene, a transcription regulatory region of a selected gene, such as a promoter, enhancer, repressor, or the like. A predetermined sequence characteristic can also be a segment of a specific binding site of a DNA-binding protein, a CpG island, a locus control region (LCR), a boundary element of a transcriptional unit, a matrix attachment region (MAR), or the like. In one aspect, such sorting of uniquely tagged polynucleotides allows massively parallel operations, such as simultaneously sequencing, genotyping, or haplotyping many thousands of genomic DNA fragments from different genomes. In another aspect, such sorting of uniquely tagged genomic DNA fragments includes generating a population of fragments enriched for one or more predetermined exons of the same gene from different genomes and comparing such enriched fragments to a reference sequence to determine fragments whose sequences vary from the reference sequence. In another aspect, such fragments having sequences that vary from the reference sequence are isolation from the population of all tagged genomic DNA fragments.

Exemplary polynucleotides that may be tagged and sorted in accordance with the invention include fragments of genomic DNA, DNA copies of RNAs, such as cDNAs, and the like. Such exemplary polynucleotides also include predetermined sets of genes or exons or other sequence segments of interest, such as promoter regions and the like, that may be selectively amplified from populations of DNA, such as genomic DNA or cDNA libraries. Exemplary techniques for selectively amplifying and/or isolating selected sequences of DNA from complex mixtures are disclosed in the following references: Faham et al, U.S. patent publication 2003/0104459; Dahl et al, Nucleic Acids Research, 33(8): e71 (2005); Stenberg et al, Nucleic Acids Research, 33(8): e72 (2005); Schouten et al, Nucleic Acids Research, 30(12): e57 (2002); Eldering et al, Nucleic Acids Research, 31(23): e153 (2003); and the like. Thus, using such techniques, a plurality of segments of genomic DNA from multiple individuals may be analyzed simultaneously in a single mixture. In one aspect, such a plurality may be in the range of from ten to several hundred, e.g. 500, or from ten to 200, or from ten to 100. In another aspect, such mixture may be formed from multiple individuals in the range of from ten to several thousand, e.g. 3000, or from ten to 1000, or from ten to several hundred, e.g. 200, 300, 400 or 500.

Figure 1B:
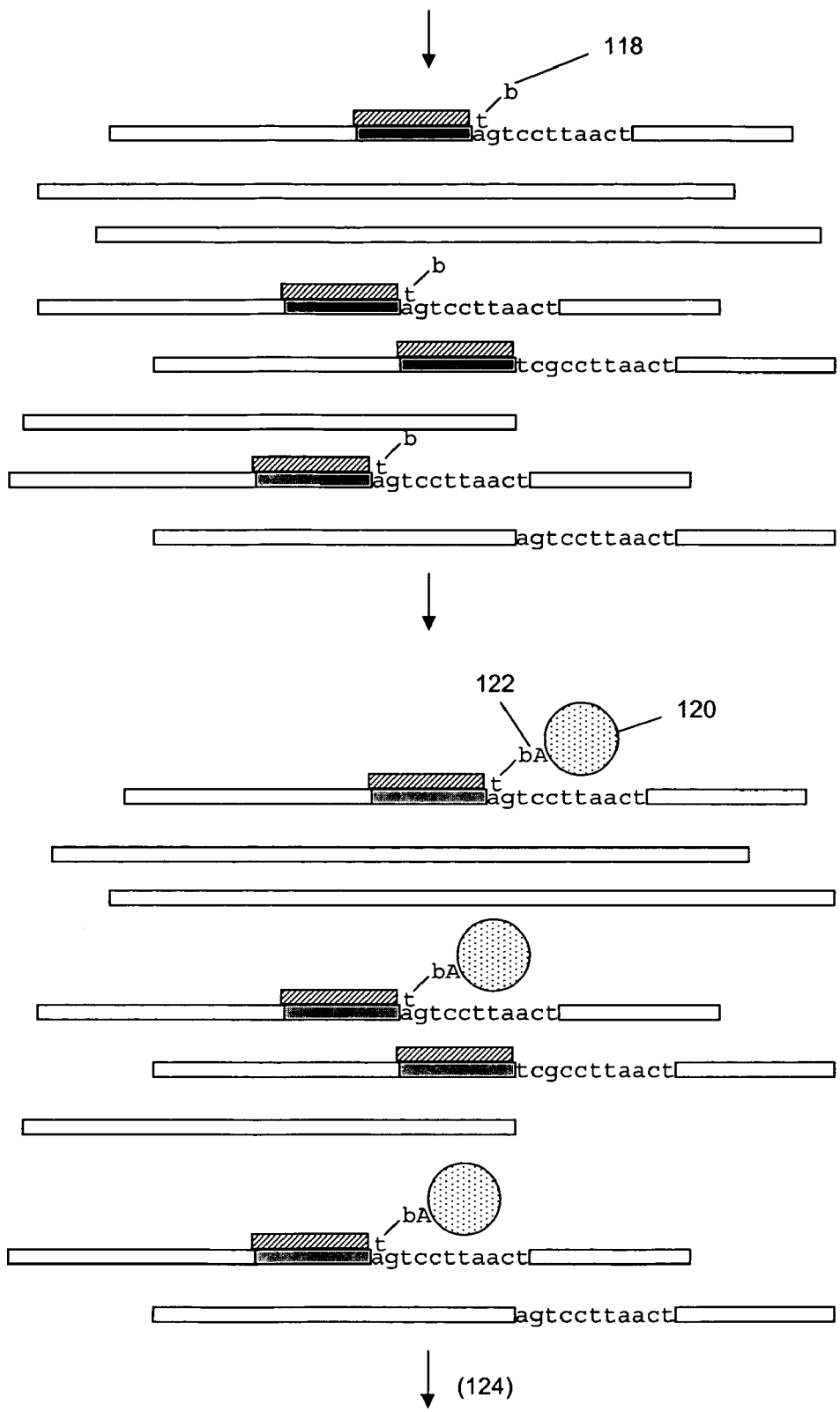
Figure 1C:
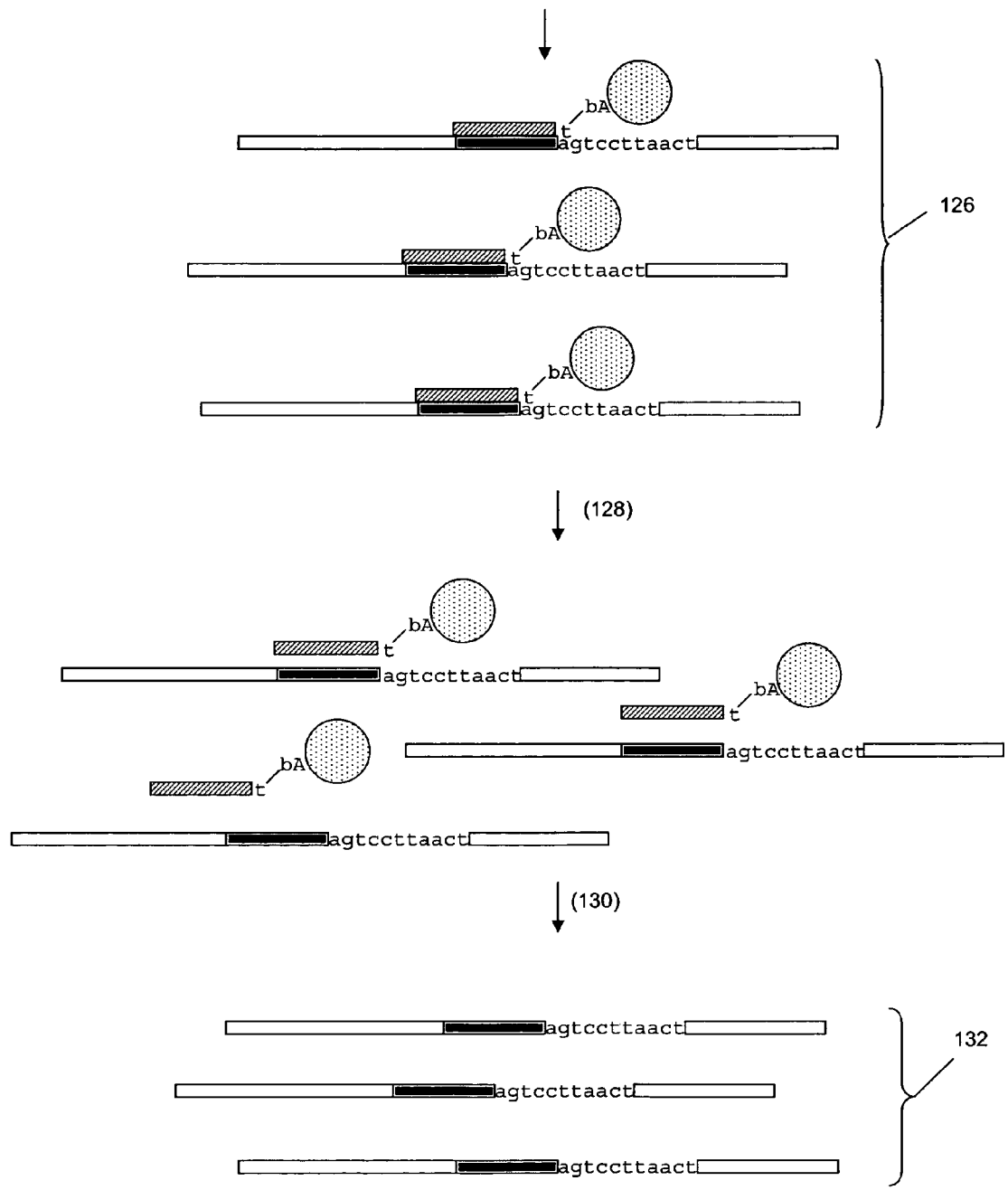

One aspect of the complexity-reducing method of the invention is illustrated in FIGS. 1A-1C. Population of polynucleotides (100), sometimes referred to herein as a parent population, includes sequences having a known sequence region that may be used as a primer binding site (104) that is immediately adjacent to (and upstream of) a region (102) that may contain one or more SNPs. Primer binding site (104) has the same, or substantially the same, sequence whenever it is present. That is, there may be differences in the sequences among the primer binding sites (104) in a population, but the primer selected for the site must anneal and be extended by the extension method employed, e.g. DNA polymerase extension. Primer binding site (104) is an example of a predetermined sequence characteristic of polynucleotides in population (100). Parent population (100) also contains polynucleotides (106) that do not contain either a primer binding site (104) or polymorphic region (102)and polynucleotides (108) that do not contain a primer binding site (104), but do contain polymorphic region (102). In one aspect, the invention provides a method for isolating sequences from population (100) that have primer binding sites (104) and polymorphic regions (102). This is Accomplished by annealing (110) primers (112) to polynucleotides having primer binding sites (104) to form primer-polynucleotide duplexes (113). After primers (112) are annealed, they are extended (114) to incorporate a predetermined terminator having a capture moiety. Extension may be effected by polymerase activity, chemical or enzymatic ligation, or combinations of both. A terminator is incorporated so that successive incorporations (or at least uncontrolled successive incorporations) are prevented. A primer of a primer-polynucleotide duplexes, such as that illustrated by (113), can be fully complementary to its polynucleotide, or it can be complementary only at a portion of its 3' end, for example, complementary over a portion of sufficient length so that a DNA polymerase can extend the primer. In the latter example, the 5' end of the primer can contain other sequences that are not complementary to the polynucleotide, e.g. as disclosed in Faham et al, U.S. patent publication 2003/0104459, or the like.

This step of extension may also be referred to as "template-dependent extension" to mean a process of extending a primer on a template nucleic acid that produces an extension product, i.e. an oligonucleotide that comprises the primer plus one or more nucleotides, that is complementary to the template nucleic acid. As noted above, template-dependent extension may be carried out several ways, including chemical ligation, enzymatic ligation, enzymatic polymerization, or the like. Enzymatic extensions are preferred because the requirement for enzymatic recognition increases the specificity of the reaction. In one aspect, such extension is carried out using a polymerase in conventional reaction, wherein a DNA polymerase extends primer (112) in the presence of at least one terminator labeled with a capture moiety. Depending on the embodiment, there may be from one to four terminators (so that synthesis is terminated at any one or at all or at any subset of the four natural nucleotides). For example, if only a single capture moiety is employed, e.g. biotin, extension may take place in four separate reactions, wherein each reaction has a different terminator, e.g. biotinylated dideoxyadenosine triphosphate, biotinylated dideoxycytidine triphosphate, and so on. On the other hand, if four different capture moieties are employed, then four terminators may be used in a single reaction. Preferably, the terminators are dideoxynucleoside triphosphates. Such terminators are available with several different capture moieties, e.g. biotin, fluorescein, dinitrophenol, digoxigenin, and the like (Perkin Elmer Lifesciences). Preferably, the terminators employed are biotinylated dideoxynucleoside triphosphates (biotin-ddNTPs), whose use in sequencing reactions is described by Ju et al, U.S. Pat. No. 5,876,936, which is incorporated by reference. In one aspect of the invention, four separate reactions are carried out, each reaction employing only one of the four terminators, biotin-ddATP, biotin-ddCTP, biotin-ddGTP, or biotin-ddTTP. In further preference, in such reactions, the ddNTPs without capture moieties are also included to minimize misincorporation. The captured polynucleotides contain the primer extended by a single dideoxynucleotide and thereby selects for the templates with the complementary base at the first position. Thus, the complexes captured with dideoxythymidine will have all the templates with an initial adenine, which is of lower complexity than the original collection of templates.

As illustrated in FIG. 1B, primer (112) is extended to incorporate a biotinylated dideoxythymidine (118), after which primer-polynucleotide duplexes having the incorporated biotins are captured with a capture agent, which in this illustration is an avidinated (122) (or streptavidinated) solid support, such as a microbead (120). Captured polynucleotides (126) are separated (124) and polynucleotides are melted (128) from the extended primers to form (130) population (132) that has a lower complexity than that of the parent population (100). Other capture agents include antibodies, especially monoclonal antibodies, that form specific and strong complexes with capture moieties. Many such antibodies are commercially available that specifically bind to biotin, fluorescein, dinitrophenol, digoxigenin, rhodamine, dansyl, and the like (e.g. Molecular Probes, Eugene, Oreg.), which may serve as capture moieties. In one aspect, a biotin is used as a capture moiety and avidin, streptavidin, or like protein, is used as a capture agent. Several biotins may be used with the method of the invention, including biotin, desthiobiotin, and the like, e.g. Haugland, Handbook of Fluorescent Probes and Research Reagents, Ninth Edition (Molecular Probes, Eugene, Oreg.).

Figure 1D:
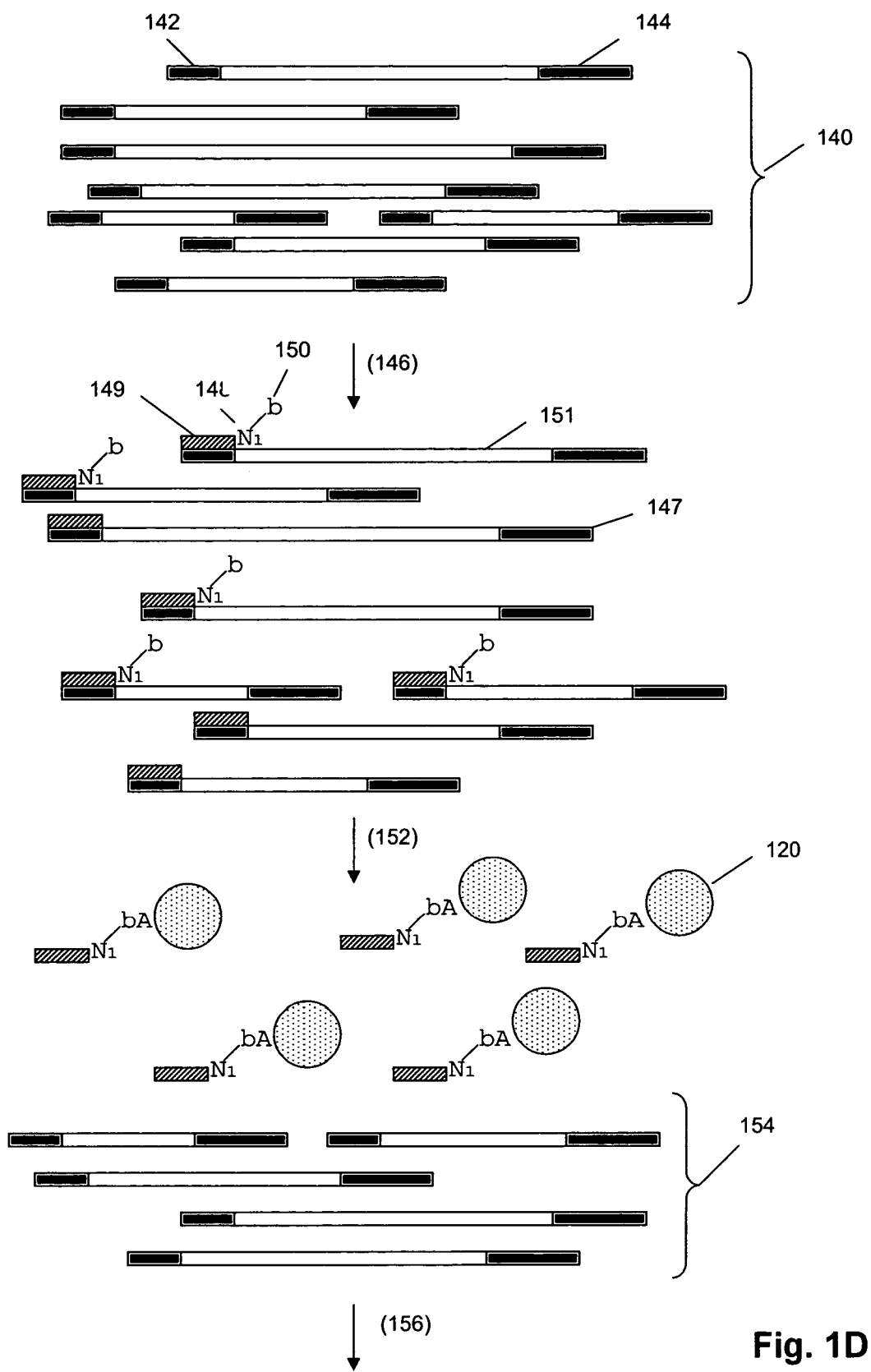
Figure 1E:
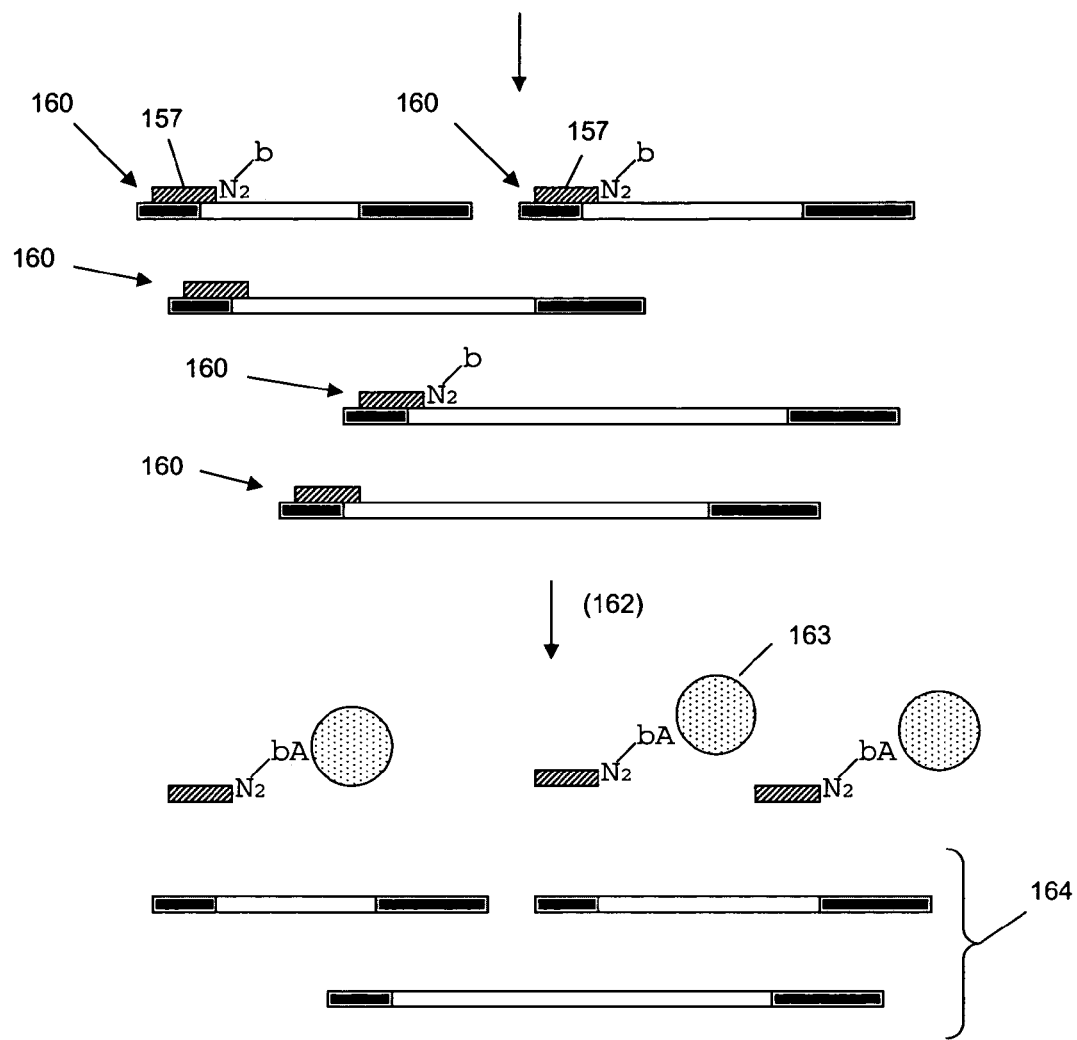

The invention also provides a method of carrying out successive selections using a set of overlapping primers of predetermined sequences to isolate a subset of polynucleotides having a common sequence, i.e. a predetermined sequence characteristic. By way of example, population (140) of FIG. 1D is formed by digesting a genome or large DNA fragment with one or more restriction endonucleases followed by the ligation of adaptors (142) and (144), e.g. as may be carried out in a conventional AFLP reactions, U.S. Pat. No. 6,045,994, which is incorporated herein by reference. Primers (149) are annealed (146) to polynucleotides (151) and extended, for example, by a DNA polymerase to incorporate biotinylated (150) dideoxynucleotide $N_1$ (148). After capture (152) with streptavidinated microbeads (120), selected polynucleotides are separated from primer-polynucleotide duplexes that were not extended (e.g. primer-polynucleotide duplex (147)) and melted to give population (154). Second primers (157) are selected so that when they anneal (156) they basepair with the first nucleotide of the template polynucleotide. That is, their sequence is selected so that they anneal to a binding site that is shifted (160) one base into the polynucleotide, or one base downstream, relative to the binding site of the previous primer. That is, in one embodiment, the three-prime most nucleotide of second primers (157) is $N_1$. In accordance with the invention, primers may be selected that have binding sites that are shifted downstream by more than one base, e.g. two bases. Second primers (157) are extended with a second terminator ("$N_2$-b" in FIG. 1E) and are captured by microbeads (163) having an appropriate capture agent to give selected population (164). Successive cycles of annealing primers, extension, capture, and melting (162) may be carried out with a set of primers that permits the isolation of a subpopulation of polynucleotides that all have the same sequence at a region adjacent to a predetermined restriction site. Preferably, after each cycle the selected polynucleotides are amplified to increase the quantity of material for subsequent reactions. In one aspect, amplification is carried out by a conventional linear amplification reaction using a primer that binds to one of the flanking adaptors and a high fidelity DNA polymerase. The number of amplification cycles may be in the range of from 1 to 10, and more preferably, in the range of from 4 to 8. Preferably, the same number of amplification cycles is carried out in each cycle of extension, capturing, and melting.

Figure 2A:
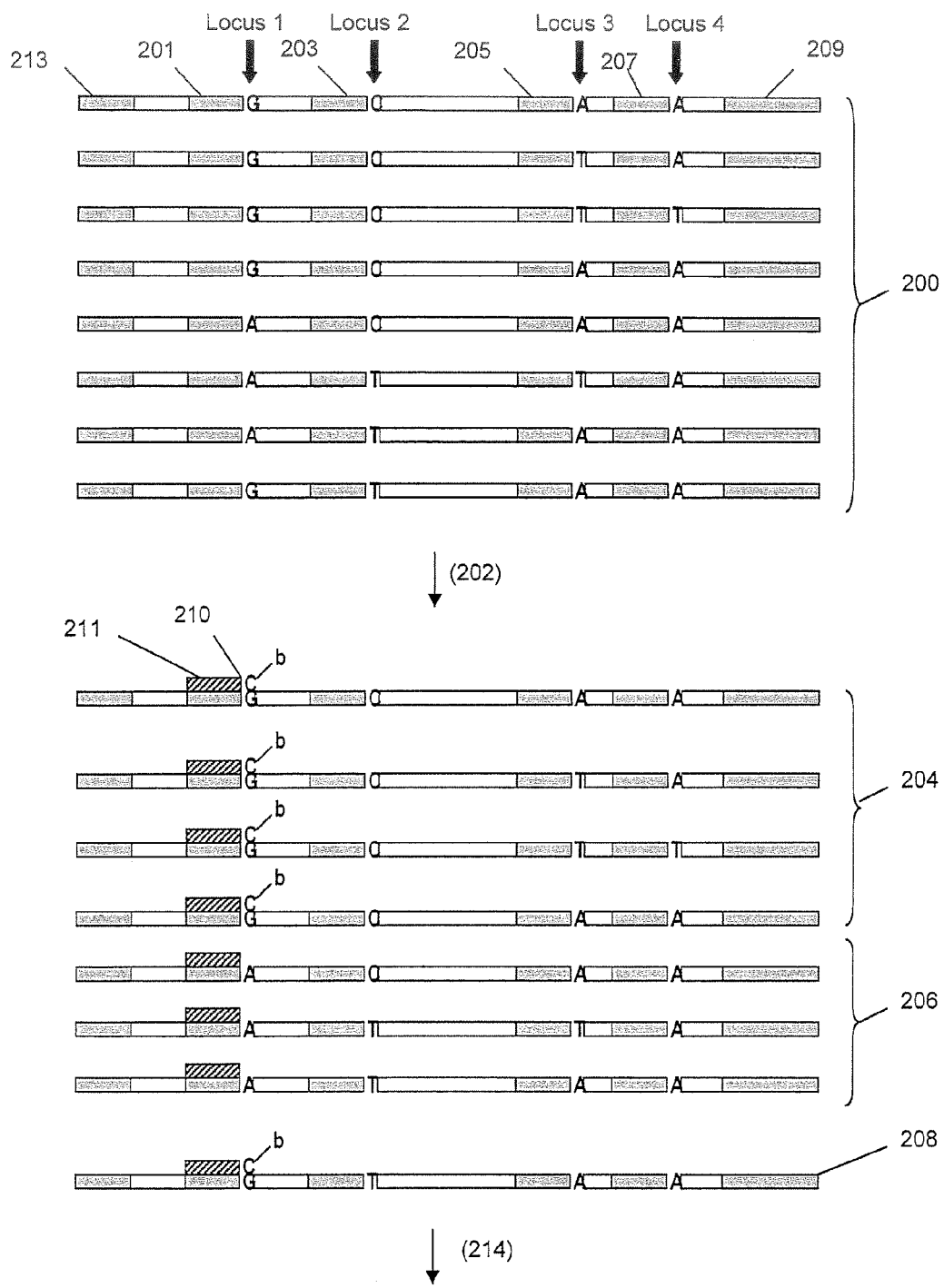
FIGS. 2A-2D illustrate the application of the invention for selecting particular haplotypes.
Figure 2B:
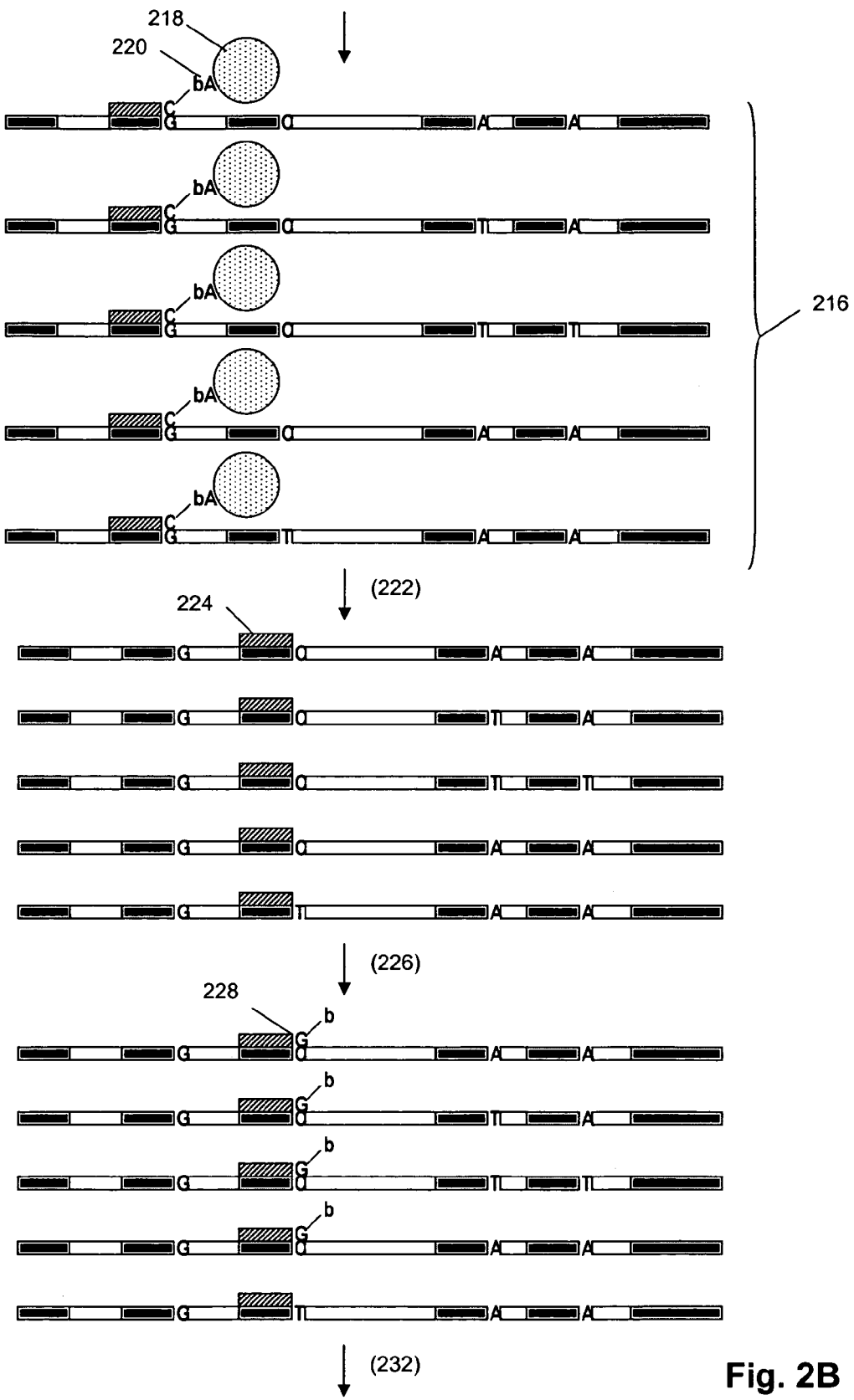
Figure 2C:
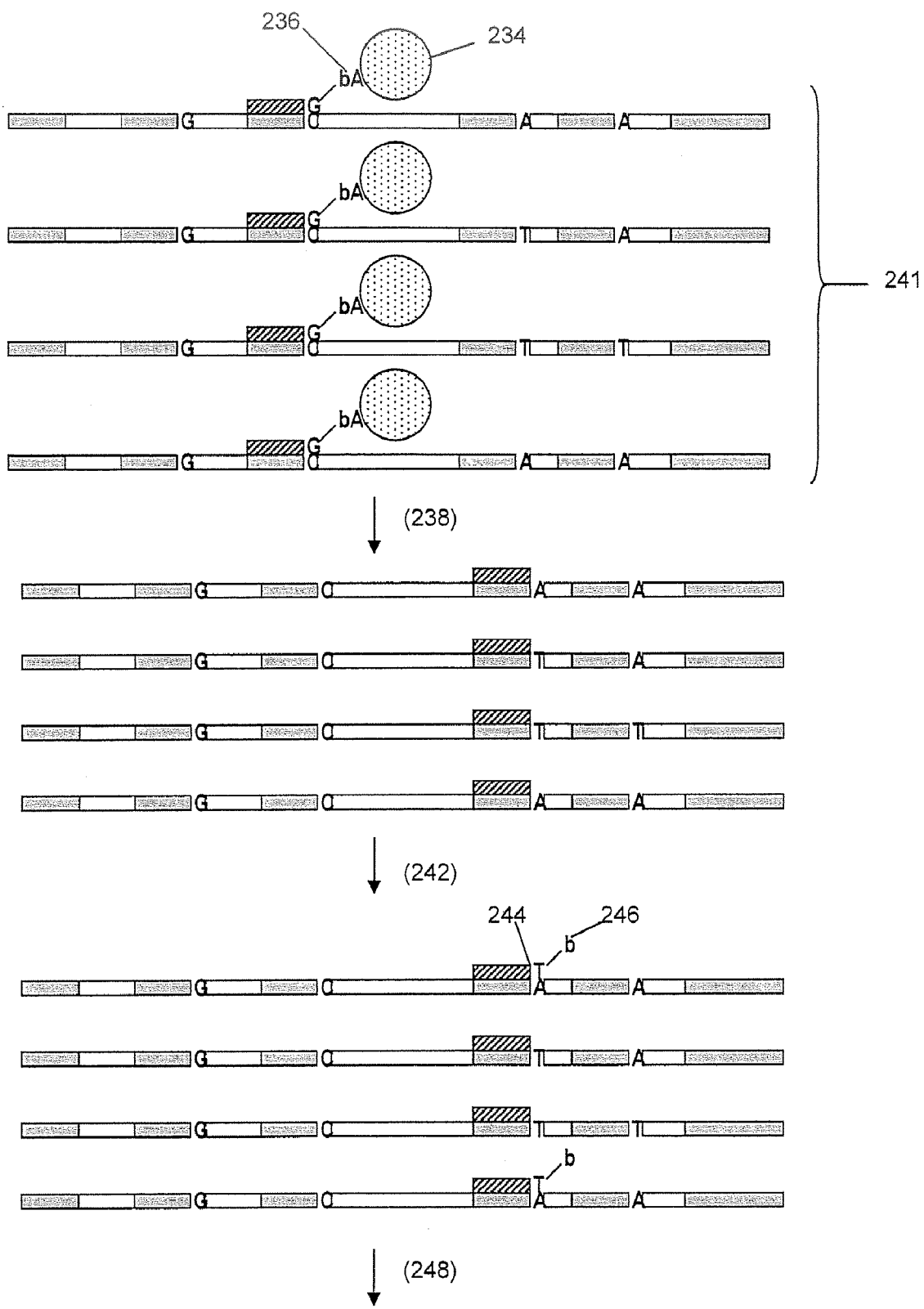
Figure 2D:
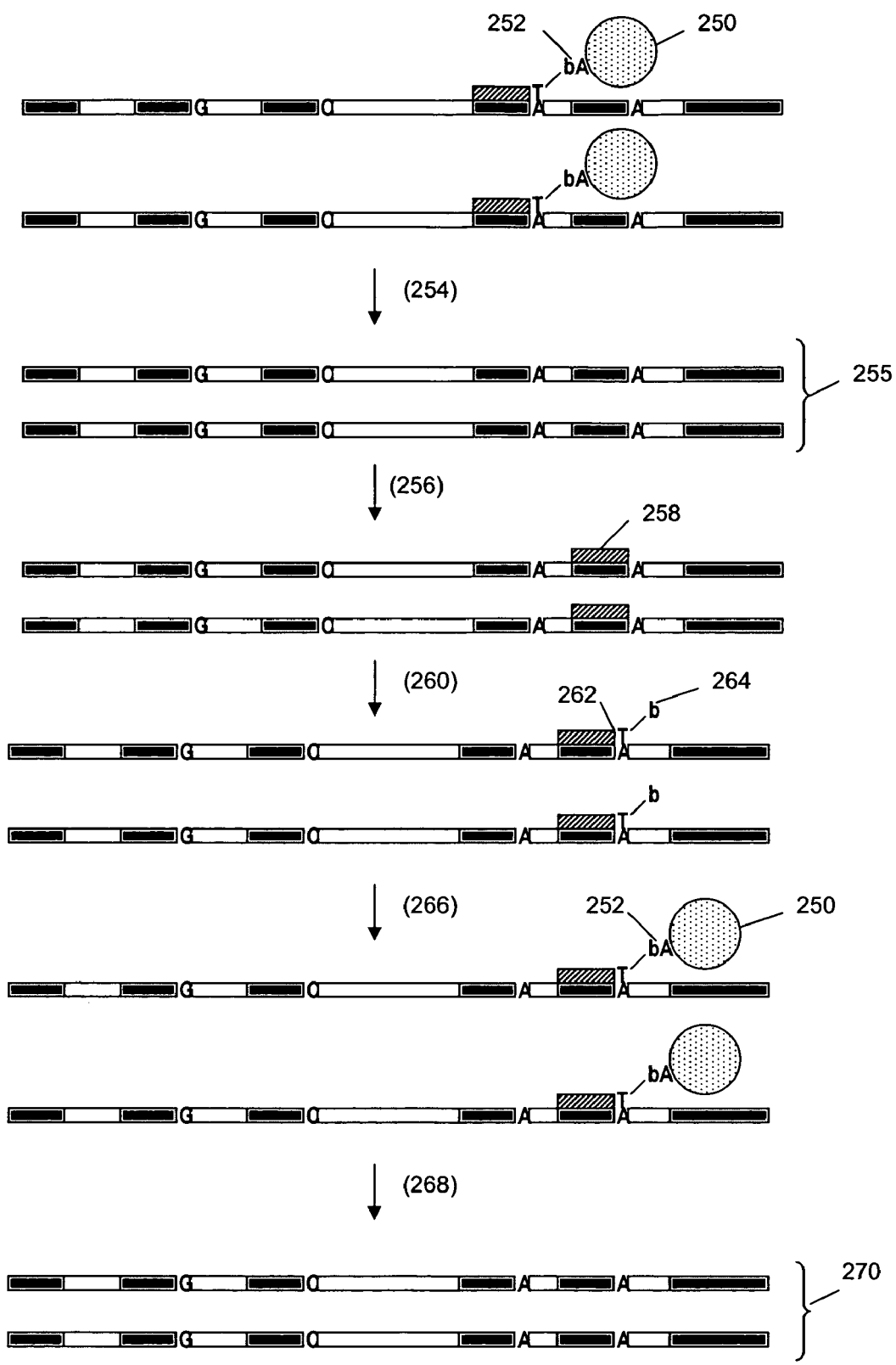

In another aspect, the invention includes a method for selecting a haplotype that comprises a sequence of SNPs adjacent to known sequence regions that are used as primer binding sites. For example, in FIG. 2A, population of polynucleotides (200) may correspond to restriction fragments of different genomes that contain polymorphic loci 1 through 4 adjacent to primer binding sites (201), (203), (205), and (207), respectively. Restriction fragments making up population (200) have adaptors (209) and (213) attached, which may be the same or different, unless oligonucleotide tags are attached to the fragments, as described more fully below. A haplotype is selected from the mixed population by successively selecting polynucleotides in accordance with the invention using primers that specifically anneal to sites (201), (203), (205), and (207). As illustrated, primer (211) anneals (202) to primer binding site (201) and is extended with a biotinylated dideoxycytidine terminator (210) since polynucleotides with a "G" at locus 1 are desired. Consequently, sequences (204) and (208), but not sequences (206) are selected (214) as described above using a solid phase support (218) having a capture agent (220). The selected polynucleotides (216) are melted and the next primer (224) is annealed (222) to binding site (203). Primers (224) are extended (226) with a biotinylated dideoxyguanosine terminator (228), because the next SNP of the desired haplotype is deoxycytidine. Solid phase supports (234) having capture agents (236) are added (232) to the reaction so that the extended primers together with their respective polynucleotides are selected (241). The process step are repeated ((238), (242), (248), (254); and (256), (260), (266), (268)) for the remaining loci producing populations ((255) and (270), respectively) until the polynucleotides containing the desired haplotype (270) is finally selected (where (244) and (262) are incorporated terminators having capture moieties (246) and (264), respectively, (258) is an annealed primer, and (252) is a capture agent attached to a solid phase support (250).

Figure 1F:
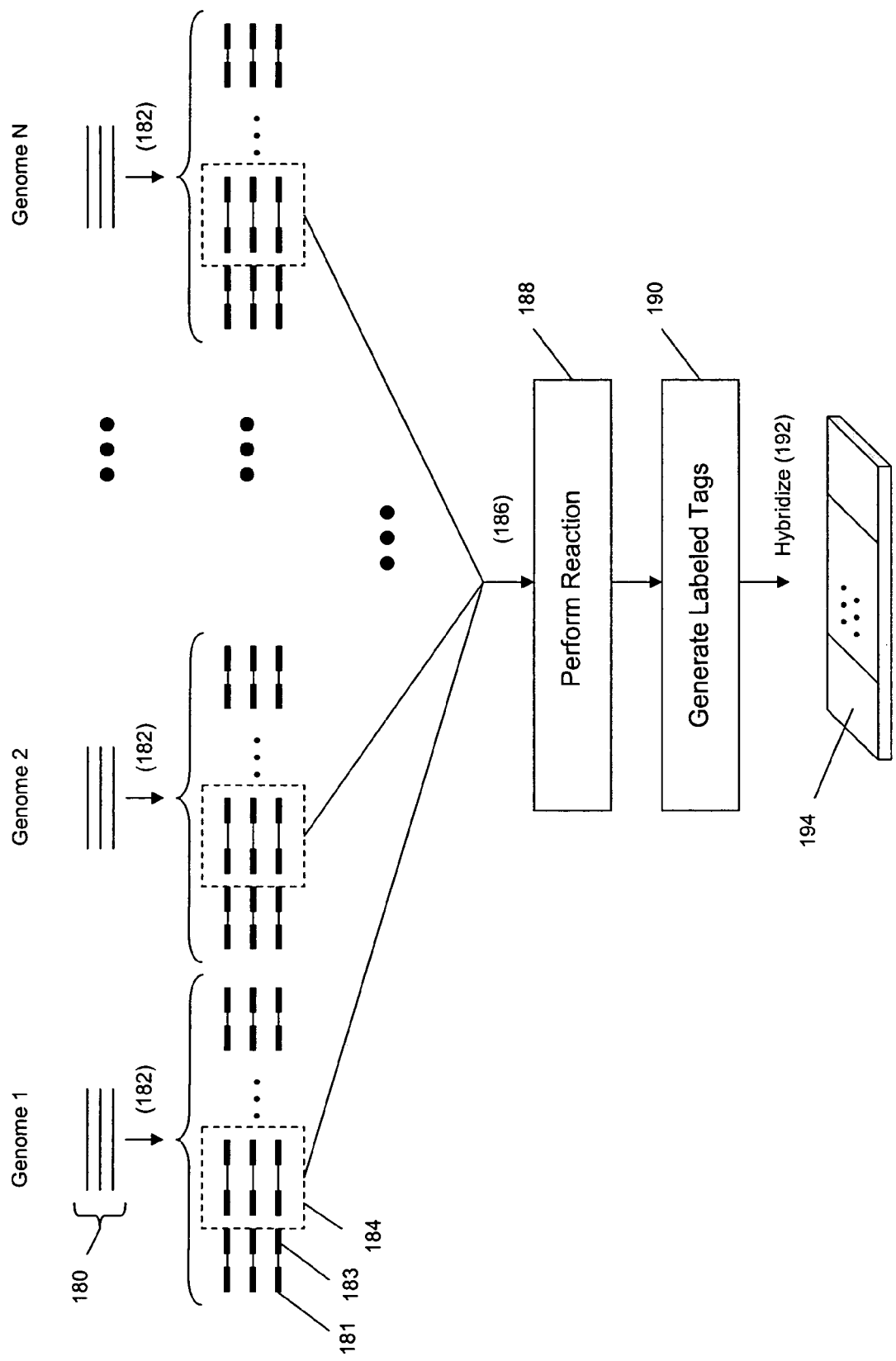

The selection methods described above may be used in another aspect of the invention in which the population of polynucleotides comprises genomes with unique tags. This aspect is illustrated in FIG. 1F. Genomes 1 through N are separately fragmented (182), e.g. in a conventional restriction endonuclease reaction, to produce fragments (180) to which adaptors (181 and 183) of the invention are attached. One of adaptors (181 or 183), examples of which are given below, contains a tag synthesized in accordance with the invention, and both adaptors (181 and 183) contain other sequences, such as primer binding sites and restriction sites, necessary to manipulate the fragments, as described above, for example. Using the sequence-specific sorting method of the invention, fragments (184) from a predetermined locus from each of the genomes are selected and combined (186) to form a reaction mixture. In other embodiments, fragments with adaptors (181 and 183) may be combined prior to selection. The isolated fragments in the reaction mixture may be analyzed (188) by a variety of techniques to identify SNPs or haplotypes, or the like, after which labeled tags are generated (190) to convey information obtained by the analytical reaction to a readout device, which preferably comprises the hybridization (192) of the labeled tags to a microarray (194), or like device. Microarray (194) contains at individual hybridization sites tag complements for every tag used to label the genomic fragments. Thus, if the analytical reaction employed identifies a nucleotide at a specific locus, i.e. a SNP, in each one of the N genomes, the SNP frequency at that locus in the population of genomes is simultaneously determined.

Virtually any population of polynucleotides may be analyzed by the method of the invention, including restriction digests, libraries of genomic fragments, cDNAs, mRNAs, or the like. Preferably, populations of polynucleotides analyzed by the invention are genomes of organisms whose sequences are known. Such genomes may be from any organism, including plant, animal, bacteria, or the like. When genomic DNA is obtained for medical or diagnostic use, it may be obtained from a wide variety of sources, including tissue biopsies, blood samples, amniotic cells, and the like. Genomic DNA is extracted from such tissues by conventional techniques, e.g. as disclosed in Berger and Kimmel, Editors, Methods in Enzymology, Vol. 152, Guide to Molecular Cloning Techniques (Academic Press, New York, 1987), or the like.

Advancing Along a Template by "Outer Cycles" of Stepwise Cleavage

The above selection methods may be used in conjunction with additional methods for advancing the selection process along a template, which allows sequencing and/or the analysis of longer sections of template sequence. A method for advancing a template makes use of type IIs restriction endonucleases, e.g. Sfa NI (5'-GCATC(5/9)), and is similar to the process of "double stepping" disclosed in U.S. Pat. No. 5,599,675, which is incorporated herein by reference. "Outer cycle" refers to the use of a type IIs restriction enzyme to shorten a template (or population of templates) in order to provide multiple starting points for sequence-based selection, as described above. In one aspect, the above selection methods may be used to isolate fragments from the same locus of multiple genomes, after which multiple outer cycle steps, e.g. K steps, are implemented to generated K templates, each one successively shorter (by the "step" size, e.g. 1-20 nucleotides) than the one generated in a previous iteration of the outer cycle. Preferably, each of these successively shortened templates is in a separate reaction mixture, so that "inner" cycles of primer extensions and sortings can be implemented of the shortened templates separately.

In another aspect, an outer cycle is implemented on a mixture of fragments from multiple loci of each of multiple genomes. In this aspect, the primer employed in the extension reaction (i.e. the inner cycle) contains nucleotides at its 3' end that anneal specifically to a particular locus, and primers for each locus are added successively and a selection is made prior to the next addition of primers for the next locus.

Assume that starting material has the following form (SEQ ID NO: 23) (where the biotin is optional):

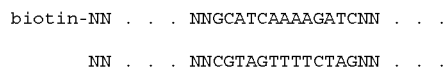

and that after cleavage with Sfa NI the following two fragments are formed (SEQ ID NO: 24):

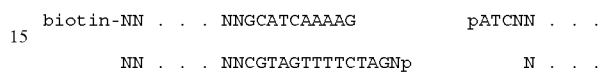

where "p" designates a 5' phosphate group. The biotinylated fragments are conveniently removed using conventional techniques. The remaining fragments are treated with a DNA polymerase in the presence of all four dideoxynucleoside triphosphates to create end on the lower strand that cannot be ligated:

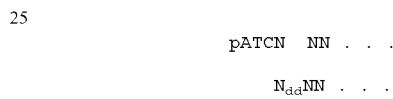

where "$N_{dd}$" represents an added dideoxynucleotide. To these ends are ligated adaptors of the following form (SEQ ID NO: 25):

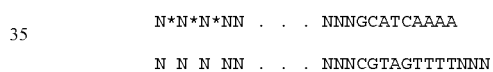

where "N*" represents a nucleotide having a nuclease-resistant linkage, e.g. a phosphorothioate. The specificity of the ligation reaction is not crucial; it is important merely to link the "top" strands together, preserving sequence. After ligation the following structure is obtained (SEQ ID NO: 26):

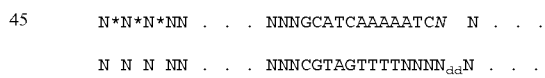

The bottom strand is then destroyed by digesting with T7 exonuclease 6, λ exonuclease, or like enzyme. An aliquot of the remaining strand may then be amplified using a first primer of the form:

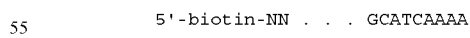

and a second primer containing a T7 polymerase recognition site. This material can be used to re-enter the outer cycle. Another aliquot is amplified with a non-biotinylated primer (5'-NN . . . GCATCAAAA) and a primer containing a T7 polymerase recognition site eventually to produce an excess of single strands, using conventional methods. These strands may be sorted using the above sequence-specific sorting method where "N" (italicized) above is G, A, T, or C in four separate tubes.

The basic outer cycle process may be modified in many details as would be clear to one of ordinary skill in the art. For example, the number of nucleotides removed in an outer cycle may vary widely by selection of different cleaving enzymes and/or by positioning their recognition sites differently in the adaptors. In one aspect, the number of nucleotides removed in one cycle of an outer cycle process is in the range of from 1 to 20; or in another aspect, in the range of from 1 to 12; or in another aspect, in the range of from 1 to 4; or in another aspect, only a single nucleotide is removed in each outer cycle. Likewise, the number of outer cycles carried out in an analysis may vary widely depending on the length or lengths of nucleic acid segments that are examined. In one aspect, the number of cycles carried out is in the range sufficient for analyzing from 10 to 500 nucleotides, or from 10 to 100 nucleotides, or from 10 to 50 nucleotides.

In one aspect of the invention, templates that differ from one or more reference sequences, or haplotypes, are sorted so that they may be more fully analyzed by other sequencing methods, e.g. conventional Sanger sequencing. For example, such reference sequences may correspond to common haplotypes of a locus or loci being examined. By use of outer cycles, actual reagents, e.g. primers, having sequences corresponding to reference sequences need not be generated. If at each extension (or inner) cycle, either each added nucleotide has a different capture moiety, or the nucleotides are added in separate reaction vessels for each different nucleotide. In either case, extensions corresponding to the reference sequences and variants are immediately known simply by selecting the appropriate reaction vessel or capture agents.

Hybridization Tags

An important feature of the invention is the use of oligonucleotide tags to uniquely label members of a population of polynucleotides. A wide variety of oligonucleotide tags may be employed. In one aspect, oligonucleotide tags are selected from the same set of oligonucleotides that have nucleotide sequences that render them mutually discriminable. That is, annealing conditions, or hybridization conditions, are available so that an oligonucleotide tag of a set forms a stable duplex with essentially only its complement and not with the complements of any other oligonucleotide tag of the same set. A set of mutually discriminable oligonucleotide tags may vary widely in sequence, length, and internal structure. In one aspect, each oligonucleotide tag of such a set differs in sequence from every other member of the same set in at least ten percent of its nucleotide positions. In another aspect, each oligonucleotide tag of such a set differs in sequence from every other member of the same set in at least fifteen percent of its nucleotide positions. Thus, in the latter example, if all of the oligonucleotide tags in a mutually discriminable set were 8 nucleotides in length, then each member would differ from every other member by at least one nucleotide.

In another aspect, oligonucleotide tags are selected from a minimally cross-hybridizing set of oligonucleotides, or assembled from oligonucleotide subunits, i.e. "words," selected from a minimally cross-hybridizing set of oligonucleotides. Construction of such minimally cross-hybridizing sets are disclosed in Brenner et al, U.S. Pat. No. 5,846, 719, and Brenner et al, Proc. Natl. Acad. Sci., 97: 1665-1670 (2000), which references are incorporated by reference. In accordance with Brenner, the sequences of oligonucleotides of a minimally cross-hybridizing set differ from the sequences of every other member of the same set by at least two nucleotides. Thus, each member of such a set cannot form a duplex (or triplex) with the complement of any other member with less than two mismatches. Preferably, perfectly matched duplexes of tags and tag complements of the same minimally cross-hybridizing set have approximately the same stability, especially as measured by melting temperature and/or dissociation temperature. Complements of hybridization tags, referred to herein as "tag complements," may comprise natural nucleotides or non-natural nucleotide analogs. Hybridization tags when used with their corresponding tag complements provide a means of enhancing the specificity, or discrimination, of hybridization. As used herein, the term minimally cross-hybridizing set also includes sets of 2-mers and 3-mers whose members differ from one another by at least a single nucleotide.

Minimally cross-hybridizing sets of oligonucleotide tags and tag complements may be synthesized either combinatorially or individually depending on the size of the set desired and the degree to which cross-hybridization is sought to be minimized (or stated another way, the degree to which specificity is sought to be enhanced). For example, a minimally cross-hybridizing set may consist of a set of individually synthesized 10-mer sequences that differ from each other by at least 4 nucleotides, such set having a maximum size of 332, when constructed as disclosed in Brenner et al, International patent application PCT/US96/09513. Alternatively, a minimally cross-hybridizing set of oligonucleotide tags may also be assembled combinatorially from subunits which themselves are selected from a minimally cross-hybridizing set. For example, a set of minimally cross-hybridizing 12-mers differing from one another by at least three nucleotides may be synthesized by assembling 3 subunits selected from a set of minimally cross-hybridizing 4-mers that each differ from one another by three nucleotides. Such an embodiment gives a maximally sized set of $9^3$, or 729, 12-mers.

When synthesized combinatorially, a hybridization tag preferably consists of a plurality of subunits, each subunit consisting of an oligonucleotide of 2 to 10 nucleotides in length wherein each subunit is selected from the same minimally cross-hybridizing set. In such embodiments, the number of hybridization tags available depends on the number of subunits per tag and on the length of the subunits.

Comma-less Hybridization Tags

In one aspect of the invention, oligonucleotide tags are hybridized to their complementary sequences, or "anti-tags," which are attached to a solid phase support, such as a microarray. In such circumstances, it is desirable to employ oligonucleotide tags that are highly specific for anti-tags that form perfectly matched duplexes between each and every word of the tag, and that form, at best, only weakly stable duplexes with anti-tags in which words are not perfectly aligned. That is, in order to avoid spurious signals, it is desirable select sets of words (and tags constructed from them) that do not form stable duplexes when hybridized in an imperfectly aligned configuration, e.g. shifted 1 to 2, or more, bases out of perfect alignment. Sets of words with such properties may be constructed in several ways, including by inserting "commas" between words or by using words that inherently possess the above properties, i.e. which result in so-called "comma-less" tags, as discussed below. Tags of word having commas are readily constructed from the minimally cross-hybridizing sets of words disclosed by Brenner in the several references cited above. Either comma-containing or comma-less tags may be used with the invention; however, comma-less tags are preferred, as they generate the maximum degree of instability in a duplex formed after any small (e.g. 1-3 nucleotide) shift of the tag and anti-tag out of perfect alignment, also sometimes referred to herein as a "change of phase."

Figure 3A:
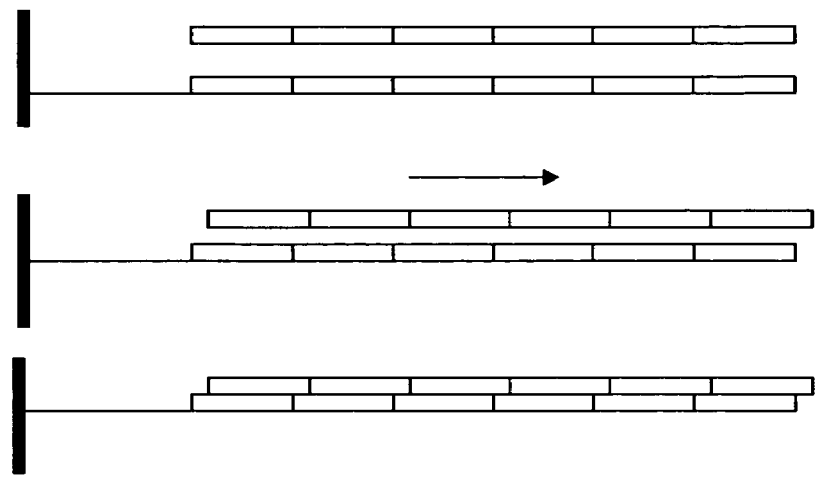
FIGS. 3A-3D illustrate hybridization tags with "commas" and a hybridization tag with the "comma-less" property.

As mentioned above, in tags synthesized combinatorially from shorter oligonucleotide "words," stable duplexes may form between a tag and its complement, even though the "words" are not perfectly aligned. As illustrated in FIG. 3A, an oligonucleotide tag consisting of words may align perfectly with its complement to form a perfectly matched duplex. However, with some selections of words, there may be other tags in the same repertoire that also form stable duplexes, even though the tag is shifted, or out of alignment, by one or more bases with a complement. The stability of such spurious pairings is very close to that of the perfectly aligned pairings, making it difficult to discriminate between correctly hybridized tags and incorrectly hybridized tags.

Figure 3B:
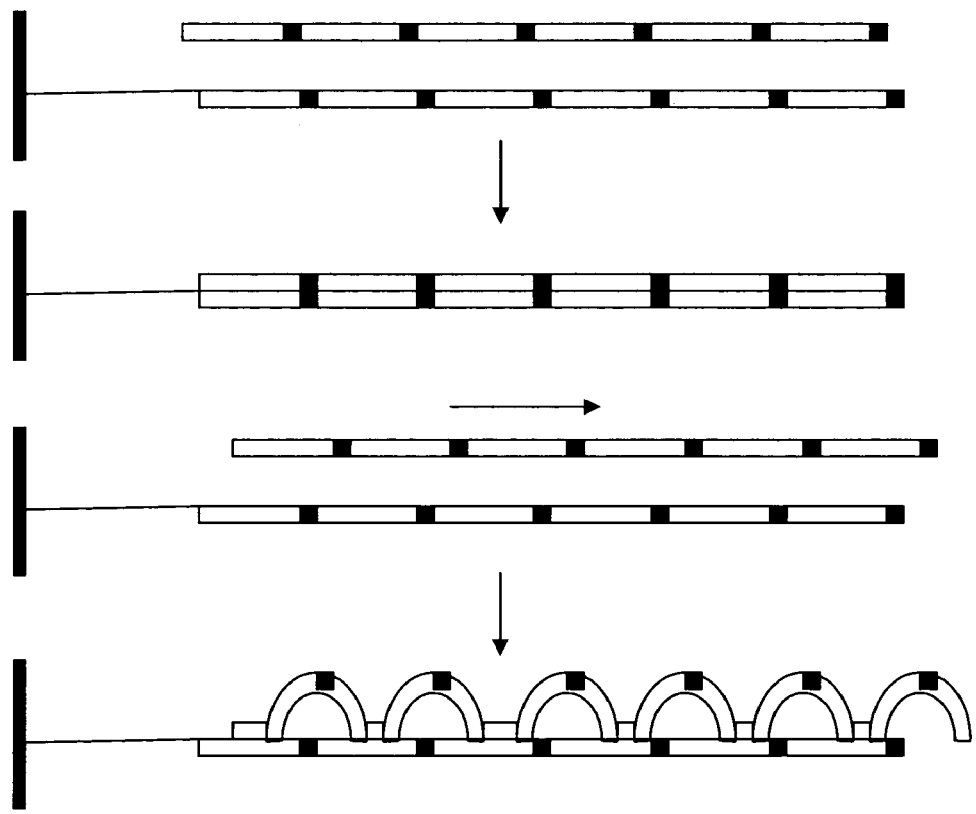

Such spurious hybridizations can be eliminated by designing tags that have large numbers of mismatches whenever the tag and its complement are shifted one or more bases away from the perfectly aligned configuration. As mentioned above, such designs can be accomplished by either introducing "commas" between words, or by designing words that inherently have the property that any shift out of perfect alignment introduces large numbers of stability-destroying mismatches. In its simplest form, "commas" may be one or more nucleotides introduced between the words of a tag, as illustrated in FIG. 3B. For example, the commas of a tag may consist of G's, while the words may consist of only A's, T's, and C's. Thus, for a perfectly matched duplex to form (i) the commas must be aligned, and (ii) the words of a tag must each be the complement of the words of its anti-tag. If neither of these conditions is met, then no duplex will form, or if it does form, its stability will be vastly lower than that of the perfectly aligned and matched tags.

Figure 3C:
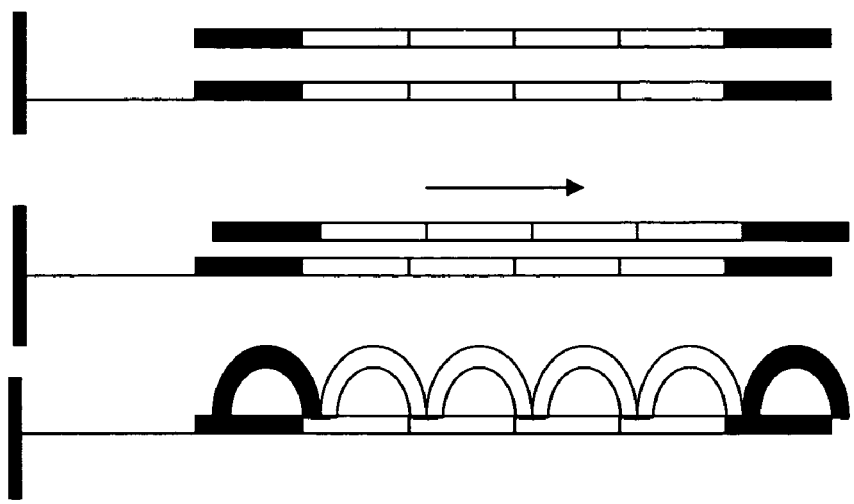

"Commas" may also take the form of words, as illustrated in FIG. 3C. Again, by way of example, the end words shown in black may consist of G's, whereas the internal words (shown in white) may consist of A's, C's, and T's. This constrains a tag and its complement to be correctly aligned. As above, absence perfect alignment, the stability of any duplex that forms will be vastly lower than that of a perfectly aligned tag and its complement.

Figure 3D:
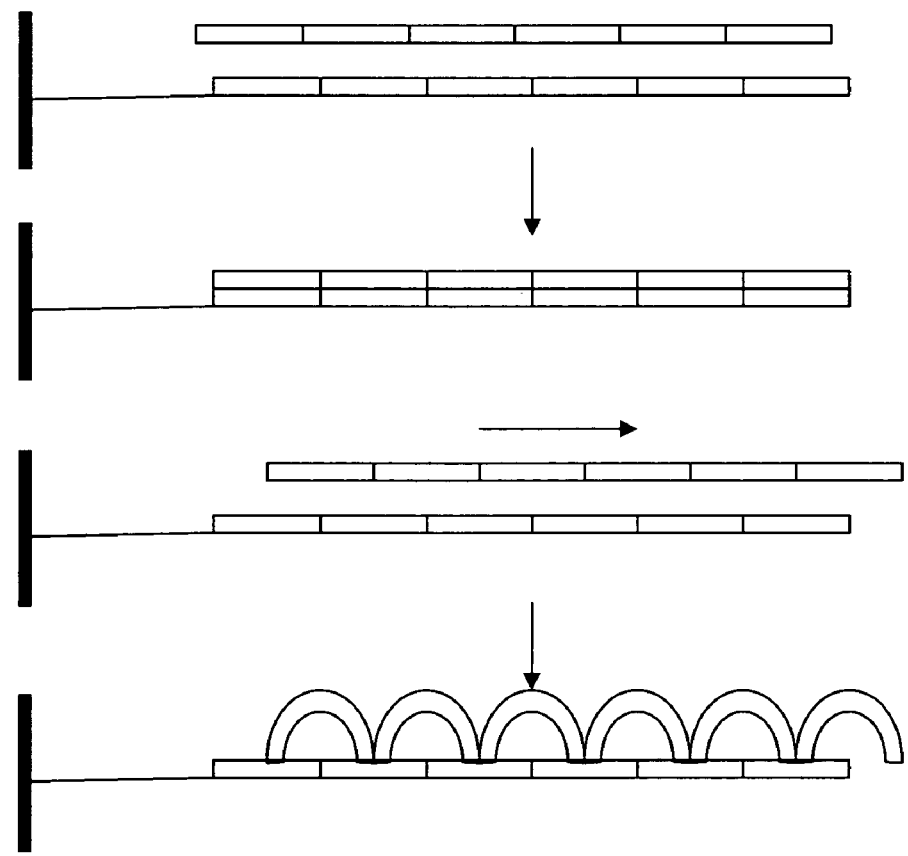

Finally, repertoires of tags without commas may be constructed from words that have the same properties as tags with commas. Such tags with the "comma-less" property are illustrated in FIG. 3D. That is, in order to form a perfectly matched duplex between a tag and a complement, the two must be perfectly aligned. Words for a repertoire of comma-less tags may be constructed in a wide variety of lengths, e.g. such words may have lengths in the range of from 4 to 10 nucleotides, and may consist of natural or non-natural nucleotides. In one aspect, words are construct from the four natural nucleotides, A, C, G, and T, whenever the resulting tags are operated on by enzymes. In another aspect, words may be constructed from nucleotides selected from the group consisting of A, C, G, T, and I, when the resulting tags (or anti-tags) are not processed by enzymes. Anti-tags synthesized on a solid phase support may typically be constructed from a wider variety of nucleotides than tags that are processed by enzymes. In one aspect of the invention, comma-less tags may be constructed from the following words.

Consider doublets of the four natural bases. Four sets of such doublets, 16 in all, can be defined as follows.

| I | II | III | IV |
|---|----|-----|-----|
| GT | CT | AT | AA |
| TG | TC | TA | TT |

-continued

| I | II | III | IV |
|---|----|-----|-----|
| AC | AG | CG | CC |
| CA | GA | GC | GG |

In each set, all four differ in both positions from all the other members of the set, but when the four different sets are compared with each other, one base is held in common with one member of the other set. For example, in set I, eight different words can be created by combining doublets from set I with doublets from set II in the I-II order and the II-I order. Since each of these sets contain doublets that are the reverse complements of the other, the combinations are made such that none of I-II four-base words are the inverse complements of the II-I four-base words. Thus, if the I-II words are selected as follows: GTCT, TGTC, ACAG, and CAGA, then the II-I words can be defined only as follows:

| AGCA | or | AGGT |
| GAAC |    | GATG |
| CTTG |    | CTAC |
| TCGT |    | TCCA | an arrangement which conserves the constraint that the members of each set differs by three bases from any member of the same set. From the above sets, several sets of words for comma-less tags can be constructed. Taking the first two sets, an "A" to the end of each words of the first set, and a "T" to the end of each word of the second set to give the following:

| AGCAT | GTCTA |
| GAACT | TGTCA |
| CTTGT | ACAGA |
| TCGTT | CAGAA |

Although the same process does not work with sets III and IV above because in III the doublets are self-complementary, further sets of words can be created by switching the I-II into II-I and vice versa, and adding the bases as above, which gives:

| CTGTA | CAAGT |
| TCTGA | ACGAT |
| AGACA | TGCTT |
| GACAA | GTTCT |

For tags not used in enzymatic processing, such as anti-tags synthesized on a solid phase support, the following sets employing deoxyinosine may be employed:

| AICAT | GTCTA |
| GAACT | TGTCA |
| CTTGT | ACAGA |

-continued

| | |
|---|---|
| TCITT | CAGAA |
| and | |
| CTGTA | CAAGT |
| TCTGA | ACIAT |
| AGACA | TICTT |
| GACAA | GTTCT |

Further sets of words for constructing comma-less tags are listed in FIG. 4.

Tag Complements, Hybridization and Readout

Preferably, tag complements are synthesized on the surface of a solid phase support, such as a microscopic bead or a specific location on an array of synthesis locations on a single support, such that populations of identical, or substantially identical, sequences are produced in specific regions. That is, the surface of each support, in the case of a bead, or of each region, in the case of an array, is derivatized by copies of only one type of tag complement having a particular sequence. The population of such beads or regions contains a repertoire of tag complements each with distinct sequences. As used herein in reference to hybridization tags, tag complements, and synthesis tags, the term "repertoire" means the total number of different tags or tag complements in a given set or population.

Solid phase supports containing tag complements may take a variety of forms, e.g. particulate, single-piece and planar, such as a glass slide, and may be composed of a variety of materials, e.g. glass, plastic, silicon, polystyrene, or the like. Particulate solid phase supports include microspheres, particularly fluorescently labeled microspheres, e.g. Han et al, Nature Biotechnology, 19: 631-635 (2001); Kettman et al, Cytometry, 33: 234-243 (1998); and the like. Preferably, hybridization tags are detected by hybridizing them to their complementary sequences on a conventional microarray. Such microarrays may be manufactured by several alternative techniques, such as photo-lithographic optical methods, e.g. Pirrung et al, U.S. Pat. No. 5,143,854, Fodor et al, U.S. Pat. Nos. 5,800,992; 5,445,934; and 5,744,305; fluid channel-delivery methods, e.g. Southern et al, Nucleic Acids Research, 20: 1675-1678 and 1679-1684 (1992); Matson et al, U.S. Pat. No. 5,429,807, and Coassin et al, U.S. Pat. Nos. 5,583,211 and 5,554,501; spotting methods using functionalized oligonucleotides, e.g. Ghosh et al, U.S. Pat. No. 5,663,242; and Bahl et al, U.S. Pat. No. 5,215,882; droplet delivery methods, e.g. Caren et al, U.S. Pat. No. 6,323,043; Hughes et al, Nature Biotechnology, 19: 342-347 (2001); and the like. The above patents disclosing the synthesis of spatially addressable microarrays of oligonucleotides are hereby incorporated by reference. Microarrays used with the invention contain from 50 to 500,000 hybridization sites; or from 100 to 250,000 hybridization sites; or from 100 to 40,000 hybridization sites; and preferably, they contain from 100 to 32,000 hybridization sites; or from 100 to 20,000 hybridization sites; or from 100 to 10,000 hybridization sites.

Guidance for selecting conditions and materials for applying labeled oligonucleotide probes to microarrays may be found in the literature, e.g. Wetmur, Crit. Rev. Biochem. Mol. Biol., 26: 227-259 (1991); DeRisi et al, Science, 278: 680-686 (1997); Wang et al, Science, 280: 1077-1082 (1998); Duggan et al, Nature Genetics, 21: 10-14 (1999); Schena, Editor, Microarrays: A Practical Approach (IRL Press, Washington, 2000); Hughes et al (cited above); Fan et al, Genomics Research, 10: 853-860 (2000); and like references. These references are hereby incorporated by reference. Typically, application of hybridization tags to a solid phase support includes three steps: treatment with a pre-hybridization buffer, treatment with a hybridization buffer that includes the probes, and washing under stringent conditions. A pre-hybridization step is employed to suppress potential sites for non-specific binding of probe. Preferably, pre-hybridization and hybridization buffers have a salt concentration of between about 0.8-1.2 M and a pH between about 7.0 and 8.3. Preferably, a pre-hybridization buffer comprises one or more blocking agents such as Denhardt's solution, heparin, fragmented denature salmon sperm DNA, bovine serum albumin (BSA), SDS or other detergent, and the like. An exemplary pre-hybridization buffer comprises 6× SSC (or 6× SSPE), 5× Denhardt's solution, 0.5% SDS, and 100 µg/ml denatured, fragmented salmon sperm DNA, or an equivalent defined-sequence nucleic acid. Another exemplary pre-hybridization buffer comprises 6×-SSPE-T (0.9 M NaCl, 60 mM NaH2PO4, 6 mM EDTA (pH 7.4), 0.005% Triton X-100) and 0.5 mg/ml BSA. Pre-hybridization and hybridization buffers may also contain organic solvents, such as formamide to control stringency, tetramethylammonium chloride to negate base-specific effects, and the like. An exemplary hybridization buffer is SSPE-T and the desired concentration of isostringency probe. After hybridization, unbound and non-specifically bound isostringency probe is removed by washing the detection support under stringent conditions. Preferably, stringency of the wash solution is controlled by temperature, organic solvent concentration, or salt concentration. More preferably, the stringency of the wash conditions are determined to be about 2-5° C. below the melting temperature of the isostringency probes at the salt concentration and pH of the wash solution. Preferably, the salt concentration of the wash solution is between about 0.01 to 0.1 M.

Instruments for measuring optical signals, especially fluorescent signals, from labeled tags hybridized to targets on a microarray are described in the following references which are incorporated by reference: Stem et al, PCT publication WO 95/22058; Resnick et al, U.S. Pat. No. 4,125,828; Kamaukhov et al, U.S. Pat. No. 354,114; Trulson et al, U.S. Pat. No. 5,578,832; Pallas et al, PCT publication WO 98/53300; Brenner et al, Nature Biotechnology, 18: 630-634 (2000); and the like.

When tag complements are attached to or synthesized on microbeads, a wide variety of solid phase materials may be used with the invention, including microbeads made of controlled pore glass (CPG), highly cross-linked polystyrene, acrylic copolymers, cellulose, nylon, dextran, latex, polyacrolein, and the like, disclosed in the following exemplary references: Meth. Enzymol., Section A, pages 11-147, vol. 44 (Academic Press, New York, 1976); U.S. Pat. Nos. 4,678,814; 4,413,070; and 4,046;720; and Pon, Chapter 19, in Agrawal, editor, Methods in Molecular Biology, Vol. 20, (Humana Press, Totowa, N.J., 1993). Microbead supports further include commercially available nucleoside-derivatized CPG and polystyrene beads (e.g. available from Applied Biosystems, Foster City, Calif.); derivatized magnetic beads; polystyrene grafted with polyethylene glycol (e.g., TentaGel™, Rapp Polymere, Tubingen Germany); and the like. Generally, the size and shape of a microbead is not critical; however, microbeads in the size range of a few, e.g. 1-2, to several hundred, e.g. 200-1000 µm diameter are preferable, as they facilitate the construction and manipulation of large repertoires of oligonucleotide tags with minimal reagent and sample usage. Preferably, glycidal methacrylate (GMA) beads available from Bangs Laboratories (Carmel, Ind.) are used as microbeads in the invention. Such microbeads are useful in a variety of sizes and are available with a variety of linkage groups for synthesizing tags and/or tag complements.

Hybridization Code

In one aspect, hybridization codes of the invention consist of five bases and are assembled into hybridization tags following a procedure similar to that described in Brenner and Williams (cited above). Using synthesis tags, hybridization tags are constructed that are complements of the anti-tags attached to solid phase supports, such as microarrays. Such tags have the following form (SEQ ID NO: 9):

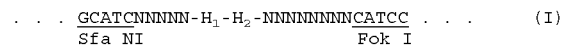

where $H_1$ and $H_2$ are words of a hybridization tag as described above, for example 4-mer words. Such words may vary in length depending on the embodiment, but generally are in the range of from 2 to 10 nucleotides in length; or they may be in the range of from 3 to 6 nucleotides in length. One factor in selecting word length is whether they are processed by restriction enzymes, such as type IIs restriction enzymes, whose recognition and cleavage characteristics may dictate word length. Using an eight-word set described above, 64 such di-words are constructed, cloned in conventional vectors, and the DNA can be obtained thereafter by PCR. These reagents containing pairs of hybridization "words" are used to form word-pair conversion adaptors, described more fully below.

The principle of successively adding words is as follows. Assuming a word is in place and that a successive word is to be added. Since the previous word can be any of the eight words, then the material to be added will need to have all possibilities in the next position, call this "$H_2$", and there would be eight such sets. Thus, when the Sfa NI site is cut the following end will result:

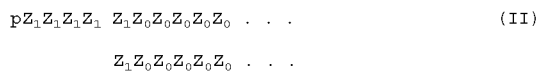

where the "$Z_1$'s" are the nucleotides of the added word, the "$Z_0$'s" are the nucleotides of the previous word, and "p" is a phosphate group. The new word is added by cutting the di-words of formula (I) at the Fok I site to give (SEQ ID NO: 10):

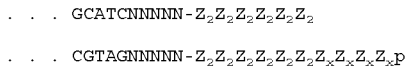

where the "$Z_2$'s" are the nucleotides of the next word, and the "$Z_x$'s" are the nucleotides of all the possible cleavage products. The cleavage product includes ends complementary to all of the possible ends of the cleavage product of formula (II). Thus, ligation of the two products permits combinatorial synthesis of the tags.

Tagging Polynucleotides

As mentioned above, an important feature of the invention is attaching oligonucleotide tags to polynucleotides, such as fragments from a genome. For simultaneous analysis of fragments from many different genomes, fragments from each different genome have the same oligonucleotide tag attached. In this manner, after a particular analytical operation has taken place on a mixture, such as extending a primer, capturing extended primers, or the like, the result on a particular fragment, or subset of fragments, may be assessed by using their respective oligonucleotide tags, e.g. by labeling, copying, and hybridizing them to a readout platform, such as a microarray. Below, an example is provided for generating a population of genomic fragments wherein fragments from each different genome have a different oligonucleotide tag attached that is comprised of oligonucleotide subunits, or words.

In one aspect of the invention, all fragments of each genome of a population of genomes are labeled with one combination of words selected from a set of eight 5-nucleotide words, or subunits. Thus, when oligonucleotide tags comprise four such words, a repertoire of 4096 oligonucleotide tags is formed; when oligonucleotide tags comprise five such words, a repertoire of 32,768 ($=8^5$) oligonucleotide tags is formed; and so on. Once each genome has a unique tag, then common-sequence fragments, e.g. a restriction fragment from a particular locus, can be selected using the method of the invention. The tags may then be used to convey information about the fragments, e.g. the identity of a nucleotide at a particular locus, to a hybridization array for a readout. One of ordinary skill in the art understands that the selection of 5-word oligonucleotide tags of five nucleotides each and the use of commaless tags are design choices that may be varied depending on the goals and constraints of any particular application. In one embodiment the following eight-word minimally cross-hybridizing set may be used to construct the above repertoire. As described below, preferably, each word is cloned in a plasmid with additional elements for aiding in the construction of oligonucleotide tags.

| AGCAT | GTCTA |
|-------|-------|
| GAACT | TGACA |
| TCTGT | ACGAA |
| CTGTT | CATCA |

Using these words, 64 di-words are prepared in separate plasmids as described in Brenner and Williams (cited above), which is incorporated by reference.

A. Single-Word Library and Counting Array Element.

In one embodiment, the single word library contains a ten-base sequence [G/T; G/T; A/T]$_3$G/T, where "x/T" is an equal mixture of the two bases "x" and "T" at a particular locus. This element encodes a repertoire of 1024 ($=2^{10}$) different sequences that permits sequences to be counted by hybridization of copies of the sequence to an array of complementary sequences, i.e. a "counting" array. This element is referred to herein as the "Counting Array" or "CAR" element. In this embodiment, about 30 copies of each genome are tagged and each is labeled with one unique sequence. Thus, if any sorted molecule is found to have a unique sequence for this array, it is not a genome difference that should have multiple sequences, and is likely to represent an error in the process which has resulted in an altered molecule. Note that however much any fragment is amplified that it will always possess the original sequences in the counting array, preserving cardinality as distinct from the concentration of DNA.

A plasmid having the following characteristics is constructed: (i) no SapI site, and (ii) a sequence of restriction sites:

```
GGGCCC . . . AGGCCT . . . GGTACC
(ApaI)      (BspE1)      (KpnI)
```

These sites each have "GG" which is absent from tags constructed from the words of the above set. Next for each word the strands of following element are synthesized (SEQ ID NO: 11):

```
5'-pCNNNNNNNNNNNGCATCNNNNN[WORD]A
3'-CCGGGNNNNNNNNNNNCGTAGNNNNN[WORD]TCCGGp
              (Sfa N1)
``` where lower case "p" represents a phosphate group. After annealing the strands, the element is cloned into the above plasmid by cleaving with ApaI and Bsp E1. Several plasmids are picked for each word and the clones are sequenced to check the accuracy of the sequence, after which one is selected for use in tag construction. Elements for the "counting" array are synthesized and also a second primer binding site which will be required for later amplification. After synthesis, the following structure is obtained (SEQ ID NO: 12):

```
3'-NNNTCCGGA[N₁₅]CCCTG[(G/T;G/T;A/T)₃G/T]GTTGCTTCTCGCCATGGNNNN

BspE1    BsmF1    CAR element      SapI    KpnI
```

Using the primer "5'-NNNAGGCCT[N₁₅]GGGAC" (SEQ ID NO: 13) the above is copied, cleaved with KpnI and BspE1, and cloned into each of the single-word plasmids. $10^4$ clones of each are isolated to make sure that all the sequences of the counting array are in the library.

This embodiment is designed to attach tags to fragments generated by cleaving with the "↓GATC" family of restriction endonucleases. These enzymes permit the generation of the fragments of several different lengths:

| Enzyme | Recognition Site | Average Fragment Length |
|---|---|---|
| Bam HI | G↓GATCC | 4 Kb |
| Bam HI + BglII | G↓GATCC + G↓GATCT | 2 Kb |
| Bst YI | R↓GATCY | 1 Kb |
| Sau 3a | ↓GATC | 256 bp |

All of these leave the same end when cleaved, namely:

```
5'-NN

NNCTAGp
``` where "p" is a phosphate group. This may be filled in with a single dGTP to give a three-base overhang:

```
5'-NNG

NNCTAGp
```

After such filling, polynucleotides or cloning vectors cut with SapI (underlined below), which leaves the following ends:

```
5'- . . . NN      GATCGAAGAGC . . .

. . . NNTAGp      GCTTCTCG . . .
``` permits efficient and directional cloning of fragments.
The final construct has the following structure:

```
. . . [ApaI site]N₁₀[SfaN1 site]N₅[word] [BspE1 site]N₁₅[BsmF1 site] [CAR] [SapI site] [KpnI site] . . .
         Primer X                          Primer Y                              Primer Z
``` were "N" are arbitrarily selected nucleotides and "CAR" is a counting array element, as described above.

B. Double-Word Libraries.

Here a library of 64 vectors is disclosed each containing one of the 64 possible two-word, or "di-word," concatenations of words from the 8-word library flanked by primer binding sites. This double-word library is then used essentially as described in Brenner and Williams (cited above) to construct oligonucleotide tags. In this embodiment, the first flanking primer binding site is that shown above as "Primer X," and the other contains a recognition site for Foki, 5'-GGATG(9/13), which contains "GG" and therefore cannot cut any of the words described above.

The following vector elements are synthesized (SEQ ID NO: 14):

```
5'-pCN₁₀[SfaN1 site]N₅[word 1][word 2]N₈CATCC
``` and (SEQ ID NO: 15):

```
3'-CCGGGN₁₀[SfaN1 site]N₅[word 1][word 2]
N₉GTAGGCTAG
``` where it is understood that the "word 1" and "word 2" refer to both word sequences and their respective complements. After annealing the above fragments to form a doublestranded element, it is cloned into a plasmid digested with ApaI and BamHI. To assure the accuracy of the incorporation, several clones of each "double word" vector are selected and sequenced. Copies of di-words may be conveniently obtained by PCR using a biotinylated X primer and another primer.

C. Tagging Genome Fragments.

In this example, a procedure is disclosed for attaching oligonucleotide tags to up to 4096 different genome for simultaneous analysis in accordance with the invention. The procedure is outlined in FIG. 5. Sixty-four groups of 64 mixtures are formed that each contain fragments from a single genome, each group of 64 being represented in the figure by arrays (502), (504), and (506) of 64 dots. This is base tier (500) of submixtures where fragments from each genome may be identified by its position in such a 64-element array, which may correspond to a well in a multi-well plate, a tube in a rack of tubes, or the like. Intermediate tier of submixtures (510) is formed by attaching a different two-word tag to each different genome, as described below. The two-word tag identifies a genome fragment by giving its location within the 64-element array of submixtures. To each group of two-word tagged fragments, indicated as $g_1AA$ to $g_{64}HH$; $g_{65}AA$ to $g_{128}HH$; and so on, a different tag A through H is attached and combined (514) to form the first mixture (520) in intermediate tier of mixtures (530). The rest of the groups of 64 genomes are treated the same to produce addition mixtures of intermediate tier (530), e.g. mixtures containing $g_{513}AA$ to $g_{576}HH$; $g_{577}AA$ to $g_{640}HH$; and so on, have words added and are combined (516) to form submixture (522); and so on. Tagged fragments in submixtures (520) to (524) each have a different word attached and are then combined (532) to form mixture (550) of tagged genomes. More specifically, the procedure may be carried out with the following steps.

About 1 ng of human DNA (about 300 copies of the haploid genome) is digested with Bst Y1 to give fragments of an average size of 1 Kb, after which ends are filled in with dGTP to give 3-base ends as described above.

The eight single word libraries, labeled A-H, are amplified and cut with SapI to generate the following single-word fragment:

64 genomes are tagged in one batch as follows. 64 reaction vessels are arranged in an 8×8 array wherein each row, 1-8, contains 8 vessels labeled A-H. To each vessel a different Bst YI-digested genome is added, after which a different single-word fragment, A-H, is added to vessels 1-8, in each row to give the following array of reaction vessels with the following single-word fragments:

| Row | 1-tube/cell of table (8 tubes/row or 64 tubes in total) | | | | | | | |
|---|---|---|---|---|---|---|---|---|
| 1 | $g_1A$ | $g_2B$ | $g_3C$ | $g_4D$ | $g_5E$ | $g_6F$ | $g_7G$ | $g_8H$ |
| 2 | $g_9A$ | $g_{10}B$ | $g_{11}C$ | $g_{12}D$ | $g_{13}E$ | $g_{14}F$ | $g_{15}G$ | $g_{16}H$ |
| 3 | $g_{17}A$ | $g_{18}B$ | $g_{19}C$ | $g_{20}D$ | $g_{21}E$ | $g_{22}F$ | $g_{23}G$ | $g_{24}H$ |
| 4 | $g_{25}A$ | $g_{26}B$ | $g_{27}C$ | $g_{28}D$ | $g_{29}E$ | $g_{30}F$ | $g_{31}G$ | $g_{32}H$ |
| 5 | $g_{33}A$ | $g_{34}B$ | $g_{35}C$ | $g_{36}D$ | $g_{37}E$ | $g_{38}F$ | $g_{39}G$ | $g_{40}H$ |
| 6 | $g_{41}A$ | $g_{42}B$ | $g_{43}C$ | $g_{44}D$ | $g_{45}E$ | $g_{46}F$ | $g_{47}G$ | $g_{48}H$ |
| 7 | $g_{49}A$ | $g_{50}B$ | $g_{51}C$ | $g_{52}D$ | $g_{53}E$ | $g_{54}F$ | $g_{55}G$ | $g_{56}H$ |
| 8 | $g_{57}A$ | $g_{58}B$ | $g_{59}C$ | $g_{60}D$ | $g_{61}E$ | $g_{62}F$ | $g_{63}G$ | $g_{64}H$ | where "$g_K$" is a fragment from genome K

The single-word fragments are ligated to the genome fragments to give genome fragments single-word fragments on both ends. These fragments are processed as follows so that a word is on only one end. First, the reaction constituents from every vessel in each row are so that eight mixed samples are obtained.

| Row (Tube) | Resulting Mixtures (1-tube/row) | | | | | | | |
|---|---|---|---|---|---|---|---|---|
| 1 | $g_1A$ | $g_2B$ | $g_3C$ | $g_4D$ | $g_5E$ | $g_6F$ | $g_7G$ | $g_8H$ |
| 2 | $g_9A$ | $g_{10}B$ | $g_{11}C$ | $g_{12}D$ | $g_{13}E$ | $g_{14}F$ | $g_{15}G$ | $g_{16}H$ |
| 3 | $g_{17}A$ | $g_{18}B$ | $g_{19}C$ | $g_{20}D$ | $g_{21}E$ | $g_{22}F$ | $g_{23}G$ | $g_{24}H$ |
| 4 | $g_{25}A$ | $g_{26}B$ | $g_{27}C$ | $g_{28}D$ | $g_{29}E$ | $g_{30}F$ | $g_{31}G$ | $g_{32}H$ |
| 5 | $g_{33}A$ | $g_{34}B$ | $g_{35}C$ | $g_{36}D$ | $g_{37}E$ | $g_{38}F$ | $g_{39}G$ | $g_{40}H$ |
| 6 | $g_{41}A$ | $g_{42}B$ | $g_{43}C$ | $g_{44}D$ | $g_{45}E$ | $g_{46}F$ | $g_{47}G$ | $g_{48}H$ |
| 7 | $g_{49}A$ | $g_{50}B$ | $g_{51}C$ | $g_{52}D$ | $g_{53}E$ | $g_{54}F$ | $g_{55}G$ | $g_{56}H$ |
| 8 | $g_{57}A$ | $g_{58}B$ | $g_{59}C$ | $g_{60}D$ | $g_{61}E$ | $g_{62}F$ | $g_{63}G$ | $g_{64}H$ |

The DNA of each of the eight vessels is denatured and Primer Y (pAGGCCTN₁₅GGGAC) (SEQ ID NO: 16) is added to prime the 3' tag sequence of each of the single strands as follows (SEQ ID NO: 17 AND SEQ ID NOL 18):

```
AGGCCTN₁₅GGGAC

TCCGGAN₁₅CCCTG[CAR]CTAG[fragment]CTAG[CAR]
GTCCC . . .
```

The primer is extended using 5-Me-dCTP to give the following (SEQ ID NO: 19 AND SEQ ID NO: 20):

```
[ApaI site]N₁₀[SfaN1 site]N₅[word][BspE1 site]N₁₅[BsmF1 site][CAR]
[ApaI site]N₁₀[SfaN1 site]N₅[word][BspE1 site]N₁₅[BsmF1 site][CAR]CTAp
Primer X                                Primer Y
```

```
AGGCCTN₁₅GGGAC[CAR]GATC(Me)[fragment]GATC(Me)[CAR]GTC(Me)C(Me)C(Me) . . .

TCCGGAN₁₅CCCTG[CAR]CTAG     [fragment]CTAG     [CAR]CAG    G    G    . . .
```

All of the BsmF1 sites of the fragments are protected by half methylation, except for the site to the left of the tag. When the fragments are cleaved with BsmF1, the lefthand tag is removed up to the "GATC" site, leaving the following (SEQ ID NO: 21):

```
                              ↓
              . . . GGGAC[CAR]GATC[fragment] . . .
              . . . CCCTG[CAR]CTAG[fragment] . . .
                              ↑
                              ↓
GATC[fragment]GATC[CAR][BsmF1 site][Primer Y][word]N₅[SfaN1 site][Primer X]
    [fragment]CTAG[CAR][BsmF1 site][Primer Y][word]N₅[SfaN1 site][Primer X]
```

The "GATC" overhang is filled in with dGTP and ligated to the following adaptor containing a primer binding site for sequencing (SEQ ID NO: 22):

```
           N₂₀GC^Me  ATCAG

N₂₀CG     TAGTCTAGp
```

The methylated C in the upper strand protects the lefthand site while the right hand portion of the fragments are manipulated.

Words are added as follows. First, the C's of the bottom strand are replaced with 5-methyl-C's. This is accomplished by denaturing the above fragments, priming with a biotinylated Primer X (5'-biotin-GGGCCCN₁₀[Sfa N1 site]N₅), copying with 5-Me-CTP, and removing the strands with avidinated support. The fragments are released by cleaving with Sfa N1 to give in each of the eight vessels the sequences:

```
           [fragment]GATC[CAR][Primer Y]W

[fragment]CTAG[CAR][Primer Y]WWWWWp
``` where all eight words are represented in the overhang and "W" represents a nucleotide of a word or its complement.

Next the di-word libraries are pooled, cleaved with FokI, then ligated to the above fragment to add the next word. The process is continued as outlined below until the desired number of words is added to the genomic fragments to complete the tags. Thus, by this method, 64 genomes at a time may be tagged.

Returning to the table immediately above, in each of the sixty-four 64-genome collections, a different word is added to each different row, e.g. A→Row 1, B→Row 2, etc., to produce the following mixtures:

| Row (Tube) | Resulting Mixtures | | | | | | | |
|---|---|---|---|---|---|---|---|---|
| 1 | $g_1$AA | $g_2$BA | $g_3$CA | $g_4$DA | $g_5$EA | $g_6$FA | $g_7$GA | $g_8$HA |
| 2 | $g_9$AB | $g_{10}$BB | $g_{11}$CB | $g_{12}$DB | $g_{13}$EB | $g_{14}$FB | $g_{15}$GB | $g_{16}$HB |
| 3 | $g_{17}$AC | $g_{18}$BC | $g_{19}$CC | $g_{20}$DC | $g_{21}$EC | $g_{22}$FC | $g_{23}$GC | $g_{24}$HC |
| 4 | $g_{25}$AD | $g_{26}$BD | $g_{27}$CD | $g_{28}$DD | $g_{29}$ED | $g_{30}$FD | $g_{31}$GD | $g_{32}$HD |
| 5 | $g_{33}$AE | $g_{34}$BE | $g_{35}$CE | $g_{36}$DE | $g_{37}$EE | $g_{38}$FE | $g_{39}$GE | $g_{40}$HE |
| 6 | $g_{41}$AF | $g_{42}$BF | $g_{43}$CF | $g_{44}$DF | $g_{45}$EF | $g_{46}$FF | $g_{47}$GF | $g_{48}$HF |
| 7 | $g_{49}$AG | $g_{50}$BG | $g_{51}$CG | $g_{52}$DG | $g_{53}$EG | $g_{54}$FG | $g_{55}$GG | $g_{56}$HG |
| 8 | $g_{57}$AH | $g_{58}$BH | $g_{59}$CH | $g_{60}$DH | $g_{61}$EH | $g_{62}$FH | $g_{63}$GH | $g_{64}$HH |

These are combined to form a mixture designated as $g_{1-64}$ (AA-HH), where "AA-HH" means all 64 di-words from AA to HH. The same operation is separately carried out for every one of the sixty-four batches of 64 genomes each, i.e. genomes 65-128, 129-192, . . . and 448-512 to give the following 8 mixtures:

$$g_{1-64}(AA-HH)$$

$$g_{65-128}(AA-HH)$$

$$g_{129-192}(AA-HH)$$

$$g_{193-256}(AA-HH)$$

$$g_{257-320}(AA-HH)$$

-continued $g_{321-384}$(AA-HH)

$g_{385-448}$(AA-HH)

$g_{449-512}$(AA-HH)

As above, a different word is attached to each fragment in each of the different mixtures to give the following:

| Row (Tube) | Operation | | Resulting Mixtures |
|---|---|---|---|
| 1 | A→ | $g_{1-64}$(AA-HH) | $g_{1-64}$(AAA-HHA) |
| 2 | B→ | $g_{65-128}$(AA-HH) | $g_{65-128}$(AAB-HHB) |

-continued

Figure 5:
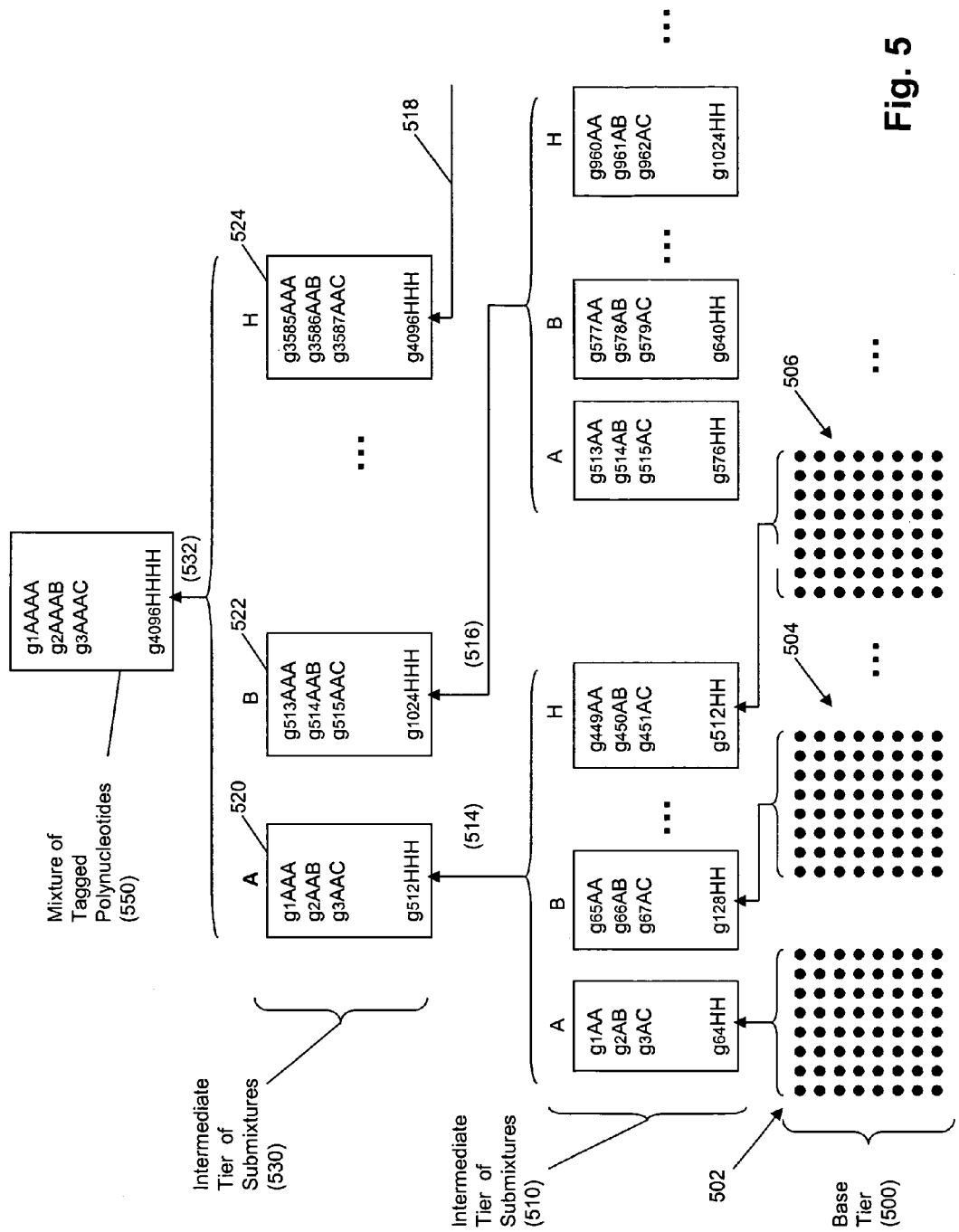
FIG. 5 illustrates tagging of polynucleotides by successive addition of oligonucleotide subunits, or "words."

| Row (Tube) | Operation | | Resulting Mixtures |
|---|---|---|---|
| 3 | C→ | $g_{129-192}$(AA-HH) | $g_{129-192}$(AAC-HHC) |
| 4 | D→ | $g_{193-256}$(AA-HH) | $g_{193-256}$(AAD-HHD) |
| 5 | E→ | $g_{257-320}$(AA-HH) | $g_{257-320}$(AAE-HHE) |
| 6 | F→ | $g_{321-384}$(AA-HH) | $g_{321-384}$(AAF-HHF) |
| 7 | G→ | $g_{385-448}$(AA-HH) | $g_{385-448}$(AAG-HHG) |
| 8 | H→ | $g_{449-512}$(AA-HH) | $g_{449-512}$(AAH-HHH) | where "AAA-HHH" means all $8^3$ (=512) tri-words from AAA to HHH. Again, a different word is attached to each fragment in each of the different three-word tagged fragment mixtures, which are then combined to form the final mixture (550), as shown in FIG. 5.

I claim:

1. A method of sorting polynucleotides having predetermined sequence characteristics, the method comprising the steps of:
    extending a primer annealed polynucleotides having predetermined sequence characteristics to incorporate a predetermined terminator having a capture moiety, wherein said predetermined terminator comprises a mixture of four kinds of terminator each complementary to a different nucleoside and wherein each kind of terminator has a different capture moiety; and
    capturing polynucleotides having extended primers by a capture agent that specifically binds to one of said different capture moiety; and
    melting the captured polynucleotides from the extended primers.

2. A method of sorting polynucleotides having predetermined sequence characteristics, the method comprising the steps of:
    providing primer annealed polynucleotides having predetermined sequence characteristics;
    separating said primer annealed polynucleotides into different mixtures, wherein each different mixture comprises a terminator complementary to a different nucleoside, said terminator having a capture moiety;
    extending said primer annealed polynucleotides in said different mixtures to incorporate said different terminator;
    capturing polynucleotides in one or more of said different mixtures having extended primers by a capture agent that specifically binds to the capture moiety; and
    melting the captured polynucleotides from the extended primers.

3. The method of claim 2 wherein said capture moiety is a biotin and wherein said terminators are each dideoxynucleotides.

4. A method of producing a subpopulation of polynucleotides having a complexity less than that of a parent population, the method comprising the steps of:
    annealing a primer to polynucleotides of a parent population to form primer-polynucleotide duplexes;
    extending the primer to incorporate a predetermined terminator having a capture moiety, wherein said predetermined terminator comprises a mixture of four kinds of terminator each complementary to a different nucleoside and wherein each kind of terminator has a different capture moiety;
    separating the primer-polynucleotide duplexes having an extended primer from the parent population by specifically binding one of said different capture moiety of the predetermined terminator to a corresponding capture agent attached to a solid phase support; and
    melting the primer-polynucleotide duplexes to form a subpopulation of polynucleotides having a complexity less than that of the parent population.

5. A method of producing a subpopulation of polynucleotides having a complexity less than that of a parent population, the method comprising the steps of:
    annealing a primer to polynucleotides of a parent population to form primer-polynucleotide duplexes;
    separating said polynucleotides of said parent population into different mixtures, wherein each different mixture comprises a terminator complementary to a different nucleoside, said terminator having a capture moiety;
    extending the primer in each of said different mixtures to incorporate said terminator;
    separating the primer-polynucleotide duplexes having an extended primer from the parent population in one or more of said different mixtures by specifically binding the capture moiety of the terminator to a capture agent attached to a solid phase support; and
    melting the primer-polynucleotide duplexes to form a subpopulation of polynucleotides having a complexity less than that of the parent population.

6. The method of claim 5 wherein said capture moiety is a biotin and wherein said terminators are each dideoxynucleotides.

7. A method of producing a population of polynucleotides having a desired complexity less than that of a parent population, the method comprising the steps of:
(a) annealing a primer to polynucleotides of a parent population to form primer-polynucleotide duplexes;
(b) extending the primer to incorporate a predetermined terminator having a capture moiety, wherein said predetermined terminator comprises a mixture of four kinds of terminator each complementary to a different nucleoside and wherein each kind of terminator has a different capture moiety;
(c) separating the primer-polynucleotide duplexes having an extended primer from the parent population by specifically binding one of said different capture moiety of the predetermined terminator to a corresponding capture agent attached to a solid phase support;
(d) melting the primer-polynucleotide duplexes to form a selected population of polynucleotides having a complexity less than that of the parent population, the selected population forming a parent population for subsequent steps; and
(e) repeating steps (a) through (d) until a selected population of the desired complexity is obtained.

8. A method of producing a population of polynucleotides having a desired complexity less than that of a parent population, the method comprising the steps of:
(a) annealing a primer to polynucleotides of a parent population to form primer-polynucleotide duplexes;
(b) separating said primer-polynucleotide duplexes into different mixtures, wherein each different mixture comprises a terminator complementary to a different nucleoside, said terminator having a capture moiety;
(c) extending the primer in each of said different mixtures to incorporate a said terminator;
(d) separating the primer-polynucleotide duplexes having an extended primer from the parent population in one or more of said different mixtures by specifically binding the capture moiety of the terminator to a capture agent attached to a solid phase support;
(e) melting the primer-polynucleotide duplexes to form a selected population of polynucleotides having a complexity less than that of the parent population, the selected population forming a parent population for subsequent steps; and
(f) repeating steps (a) through (e) until a selected population of the desired complexity is obtained.

9. The method of claim 8 wherein said capture moiety is a biotin and wherein said terminators are each dideoxynucleotides.

10. The method of claim 7 or 8 further comprising a step of replicating said selected population after said step of melting.

11. The method of claim 10 wherein during each repeating step, said primer anneals to a different primer binding site on said polynucleotides of said parent population or said selected population.

12. The method of claim 11 wherein in each successive repeating step, said different primer binding site is shifted along said polynucleotides at least one nucleotide in a primer extension direction.

13. The method of claim 11 wherein in each successive repeating step, said different primer binding site is at a different and non-overlapping locus of said polynucleotides.

14. The method of claim 13 wherein said different and non-overlapping locus is adjacent to and upstream of a single nucleotide polymorphism site.

15. A method of determining polynucleotides that have sequences that vary from that of a reference sequence, the method comprising the steps of:
(a) annealing a primer to polynucleotides of a parent population to form primer-polynucleotide duplexes;
(b) extending the primer in the presence of at least one predetermined terminator having a capture moiety, the predetermined terminator being non-complementary with the reference sequence, so that after extension primer-polynucleotide complexes that contain a polynucleotide having a sequence different from that of the reference sequence have capture moieties;
(c) separating the primer-polynucleotide duplexes having an extended primer with a capture moiety from the parent population by specifically binding the capture moiety of the predetermined terminator to a capture agent;
(d) melting captured primer-polynucleotide duplexes to form a selected population of polynucleotides having sequences different from that of the reference sequence;
(e) shortening polynucleotides of the parent population by from 1 to 20 nucleotides to form a new parent population; and
(f) repeating steps (a) through (e) until all the polynucleotides of the parent population have been sorted from polynucleotides having sequences identical to the reference sequence.

16. The method of claim 15 wherein said step of shortening includes shortening said polynucleotides of said parent population by one nucleotide.

17. The method of claim 16 wherein said step of annealing further includes separating said polynucleotides of said parent population into different mixtures prior to said step of extending so that in each different mixture said primer is extended with a terminator complementary to a different nucleoside.

18. The method of claim 17 wherein said capture moiety is a biotin and wherein said terminators are each dideoxynucleotides.

* * * * *